United States Patent [19]

Goodman et al.

[11] Patent Number: 5,093,318

[45] Date of Patent: Mar. 3, 1992

[54] IMMUNOSTIMULATING GUANOSINE DERIVATIVES AND THEIR PHARMACEUTICAL COMPOSITIONS

[75] Inventors: Michael G. Goodman, Rancho Santa Fe, Calif.; Robert Chen, Belle Mead, N.J.

[73] Assignee: Scripps Clinic and Research Foundation, La Jolla, Calif.

[21] Appl. No.: 190,694

[22] Filed: May 5, 1988

Related U.S. Application Data

[63] Continuation-in-part of Ser. No. 798,629, Nov. 15, 1985, Pat. No. 4,746,651, which is a continuation-in-part of Ser. No. 546,679, Nov. 1, 1983, Pat. No. 4,643,992.

[51] Int. Cl.⁵ .................. A61K 31/70; C07H 19/167
[52] U.S. Cl. .................................. 514/45; 536/24
[58] Field of Search .................. 536/24; 514/45; 435/240.2, 240.25; 544/260, 264, 271

[56] References Cited

U.S. PATENT DOCUMENTS 4,539,205  9/1985  Goodman et al. ............... 514/45
4,948,730  8/1990  Goodman et al. ............. 435/70.5

OTHER PUBLICATIONS

Smee, D., et al., Antimicrobial Agents and Chemotherapy, vol. 33, pp. 1487–1492, 1989.
Nagahara, K., et al., J. Med. Chem., vol. 33, pp. 407–415, 1990.

*Primary Examiner*—Johnnie R. Brown
*Assistant Examiner*—L. Eric Crane
*Attorney, Agent, or Firm*—Dressler, Goldsmith, Shore, Sutker & Milnamow, Ltd.

[57] ABSTRACT

7,8-Disubstituted guanosine nucleoside derivatives are found to be potent immune response enhancing agents in human and animal cells. 7-Substituents are heteroatom-substituted-hydrocarbyl radicals having a length greater than ethyl and less than about decyl. 8-Substituents are $=O$, $=S$, $=Se$ and $=NCN$. Compositions and methods of use are also disclosed.

13 Claims, No Drawings

5,093,318

IMMUNOSTIMULATING GUANOSINE DERIVATIVES AND THEIR PHARMACEUTICAL COMPOSITIONS

CROSS-REFERENCE TO COPENDING APPLICATION

This is a continuation-in-part of copending application Ser. No. 798,629 filed Nov. 15, 1985 now U.S. Pat. No. 4,746,651 which is a continuation-in-part of application Ser. No. 546,679, filed Nov. 1, 1983, now U.S. Pat. No. 4,643,992.

TECHNICAL FIELD

The present invention relates to immune response enhancing compounds (immunostimulants), and more particularly to guanine nucleosides derivatives that are substituted at the 7- and 8-positions of the guanine ring, as well as to compositions containing those derivatives and methods of their use.

BACKGROUND OF THE INVENTION

An animal's immune system is comprised of numerous elements that act separately and/or in concert to counteract, to eliminate, or to neutralize substances that are recognized by that system as foreign to the animal host. Generally, but not necessarily, the substance recognized as foreign by the immune system has its origin exogenous to the host. Exemplary of such exogenous substances are infectious bacteria and the by-products of their cellular activity, virus particles and their proteins, proteins injected by insect stings, and the like. In autoimmune diseases, such as rheumatoid arthritis, the host's immune system recognizes host-made proteins or self-made proteins as foreign.

The principal effectors of the immune system are the leukocytes, which include lymphocytes of thymic origin (T cells), lymphocytes produced in bone marrow (B cells), neutrophils which, inter alia, produce enzymes that make oxidizing agents such as hydrogen peroxide that have cytotoxic effects upon bacteria, and macrophages which present the foreign substance or antigen to the T cells, as well as produce a protein designated interleukin-1 that assists T cell transformation into T helper cells. Complement which is a complex mixture of proteins that acts in an ordered, cascading manner upon the foreign substance also plays a major role in immune responses.

B cells can be distinguished from T cells, inter alia, by the presence of immunoglobulins on their membrane surfaces. The immunoglobulins function as antibodies.

There are five known classes of immunoglobulins, identified as IgA, IgD, IgE, IgG, and IgM on the basis of five antigenically different heavy chain proteins which in part make up the immunoglobulin molecule. B cells also bear non-immunoglobulin cell markers, including a complement receptor (CR), a receptor for the Fc portion of immunoglobulin (FCR), I-region associated antigens (Ia), and a set of differentiation antigens (Lyb 1-7) which are identified by all antisera and are correlated with various aspects of B cell maturation and activation. These markers are useful in phenotypically identifying B cells.

While the B cell immunoglobulins act upon the foreign substance, or antigen, the T cells, and particularly helper T cells, are believed necessary to stimulate B cells to divide and to differentiate into antibody secreting cells for humoral immunity. Suppressor T cells contribute to the regulation of humoral immunity, while cytotoxic T cells and T cell mediators of delayed-type hypersensitivity are the principal effectors of cell mediated immunity.

T cells include antigens designated Lyt 1, 2, and 3 as well as L3T4 that are related to T cell functions. Helper T cell precursors are of the Lyt $1^+$, $2^-$, $3^-$, L3T4T phenotype. It is these cells which normally participate in the activation and regulation of B cells.

Helper T cells are known to assist in activation and differentiation of immunoglobulin-secreting B cells after a first message is received by the B cells from the activating antigenic agent. However, the mode by which the T cells provide the second message for B cell proliferation of activation and differentiation to the B cells is a matter of controversy.

Guanosine-3',5'-cyclic monophosphate (cGMP) has been implicated as a naturally occurring agent for providing the required second message for B cell proliferation. 8-Bromoguanosine-3',5'-cyclic monophosphate (8-BrcGMP) has been found to be a weak synthetic intracellular lymphocyte mitogen.

The immune response can be modified by artificial supression (immunosuppression) or enhancement (immunopotentiation or immunostimulation). Immunosuppression; i.e., artificially induced decreased responsiveness, can be achieved by six general methods: (1) administration of antigen, (2) administration of specific antisera or antibody, (3) use of other biologic reagents such as antilymphocyte antisera, (4) use of drugs or hormones, (5) radiation, and (6) surgical removal of lymphoid tissue. Immunopotentiation can include the administration of an agent effecting an increase in the rate at which the immune response develops, an increase in the intensity or level of the response, a prolongation of the response, or the development of a response to an otherwise non-immunogenic substance.

The agents that are known to enhance immune responses are generally termed adjuvants and can be placed into two general categories: (1) those providing general potentiation; i.e., substances that enhance both cellular and humoral immune responses for a wide variety of antigens, and (2) those providing specific potentiation, i.e., substances which enhance specific responses to certain antigens only.

Substances that can act as adjuvants can be grouped into the following categories: (1) water and oil emulsions, e.g., Freund's adjuvant, (2) synthetic polynucleotides, (3) hormones, drugs and cyclic nucleotides, (4) endotoxins, (5) proteinaceous lymphokines and monokines such as the interleukins.

A substance capable of specifically potentiating the immune response is transfer factor, a dialyzable leukocyte extract (DLE) obtained from human peripheral leukocytes. It has been reported that the transfer factor exhibits some effectiveness in patients with immunodeficiences and possible effectiveness in cancer patients and in patients with limited immunodeficiencies. However, much remains to be learned about this particular substance.

In some diseases and physiological conditions such as AIDS, X-linked agammaglobulinemias, senescence and drug-induced-immunosuppression, B cell activation and differentiation is lacking and/or exists only at a reduced level, thereby lessening the immune response of the host. These diseases and conditions are representative of immunosuppressed states. Here, enhanced activation and differentiation, if it can be effected, tends to beneficially lessen the disease manifestation and/or improve the patient's condition.

An immunopotentiated state can be illustrated by the bodily condition after vaccination. Here, the immune response is already enhanced due to an antigenic response, but could be beneficially enhanced still further to provide an improved degree and/or duration of immunity.

Co-assigned U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-1 like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned U.S. Pat. No. 4,643,992 and its corresponding published European patent application No. 83306791.1 further disclose the use of derivatives of 8-hydroxyguanine (8-oxoguanine), 7-methyl-8-oxoguanine and 7-methyl-8-thioxoguanine in modulating animal cellular responses. Further results using guanine derivatives disclosed in U.S. Pat. No. 4,539,205 are also disclosed in U.S. Pat. No. 4,643,992, as are similar results using guanine derivatives disclosed for the first time in that patent.

Still further, several papers and book chapters have been published by some of the present inventors and their co-workers relating to still further effects of compounds disclosed and claimed in U.S. Pat. No. 4,643,992. Exemplary of those published papers are Goodman, *Proc. Soc. Exp. Biol. Med.*, 179:479 (1985); Goodman, *J. Immunol.*, 136:3335 (1986); Goodman and Weigle in *Purine Metabolism In Man, Part B*, Nyhan and Thompson, eds., Plenum Press, New York, page 451 and 443 (1986); Goodman and Weigle, *J. Immunol.*, 135:3284 (1985); Goodman and Wolfert, *Immunol. Res.*, 5:71 (1986); Goodman, J. Immunol., 136:3335 (1986); Goodman, J. Immunol., 137:3753 (1986); and Goodman and Hennen, Cell. Immunol., 102:395 (1986).

BRIEF SUMMARY OF THE INVENTION 7,8-Disubstituted guanine nucleosides (guanosine derivatives) are utilized to enhance an immune response in human and animal cells. The substituted guanine nucleosides have a structure that correspond to the formula:

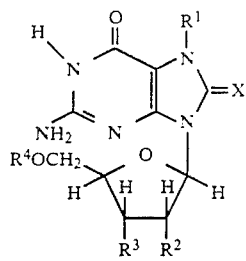

wherein X is O, S, Se or NCN; $R^1$ is a heteroatom-substituted hydrocarbyl radical that has a length greater than an ethyl group and less than a decyl group, and is free from ionic charge at physiological pH values; $R^2$ and $R^3$ are the same or different radicals selected from the group consisting of hydrogen, hydroxyl, lower alkoxy, lower alkanoyloxy and benzoxy groups, or $R^2$ and $R^3$ together constitute a lower alkylidenedioxy radical; and $R^4$ is selected from the group consisting of hydrogen, lower alkanoyl and benzoyl groups. Preferred guanosine derivatives of this invention are those in which X is O or S and $R^1$ has a total length (including its heteroatom-substituent) greater than ethyl and less than about heptyl. Particularly preferred guanosine derivatives are 7-(2-chloroethyl)-8-oxoguanosine, 7-carbethoxymethyl-8-oxoguanosine, 7-carbamoylmethyl-8-oxoguanosine, 7-methoxyethyl-8-oxoguanosine, 7-(4-nitrobenzyl)-8-oxoguanosine, 7-(4-methoxybenzyl)-8-oxoguanosine and -(2,3-dihydroxypropyl)-8-oxoguanosine. The pharmaceutically acceptable, non-toxic base addition salts of such compounds are also contemplated.

An immune response-enhancing composition that contains a diluent amount of a physiologically tolerable carrier together with a potentiating (or immunostimulating) effective amount of an above-described heteroatom-substituted guanine nucleoside derivative as an active ingredient is also contemplated by this invention.

A method of enhancing an immune response, and particularly an antigen-specific immune response is also contemplated. Here, leukocytes are contacted in an aqueous medium i.e., in culture (in vitro) or in vivo, with a composition containing an immunostimulating amount of a before-described guanine nucleoside derivative. Contact between the composition and leukocytes is maintained for a time period sufficient for the contacted cells to manifest enhancement of their immune response The leukocytes contacted are preferably B lymphocytes.

The present invention has several benefits and advantages.

One salient benefit of the present invention is that its compounds are generally more effective; i.e., provide a similar response at a lower dose or provide an enhanced response at a given dose, than previously known guanosine immunostimulants.

An advantage of the invention is that use of one of its compositions can provide the second message required for B lymphocyte activation and differentiation in response to a first (antigenic) message.

Another benefit of the invention is that an enhanced immune response can be effected in both the presence and absence of T helper cell activity. Thus, an enhanced immune response is noted in both T cell-dependent and T cell-independent systems.

Another advantage of this invention is that particular immune-suppressed or immune-deficient conditions and disease manifestations can be improved and/or lessened by use of the invention.

Still further benefits and advantages of the invention will be apparent to those skilled in the art from the discussion that follows.

Anthropomorphic descriptions such as the sending and receiving of messages by and to chemicals and cells are used herein for descriptive purposes as aids to the understanding of observed phenomena.

DETAILED DESCRIPTION OF THE INVENTION

I. Introduction

The present invention contemplates an immune response-enhancing agent (immunostimulator) that stimulates the immune system of the host mammal to which it is administered as well as stimulating leukocytes in cell culture. The immunostimulation particularly contemplated is predominantly antigen-specific for the immunizing antigen.

In studying the effects of some reportedly mitogenic guanosine derivatives, e.g., guanosine 3',5'-cyclic monophosphate and its 8-bromo derivative, it was found that a new class of low molecular weight guanine nucleoside derivatives, when present in an effective amount as the active ingredient of a composition containing a diluent amount of a physiologically tolerable carrier, provided remarkable effects in modulating responses of mammalian cells. Enhancement of antigen-specific humoral immune responses, which resulted in potent adjuvanticity, T cell replacing factor-like activity and immunoreconstitution activity are particular examples of the cellular responses that were found to be modulated. Those compounds and their methods of use are disclosed in U.S. Pat. Nos. 4,539,205 and No. 4,643,992.

The compounds of the present invention have been found to be surprisingly more active than were the compounds of the above two patents. The findings of enhanced activity were surprising for a number of reasons.

The most active compound disclosed in the above U.S. patents was 7-methyl-8-oxoguanosine (7m8oGuo), both as a leukocyte mitogen and an antigen-specific adjuvant. As will be discussed hereinbelow, mitogenicity and adjuvanticity are phenomena that are not of necessity related.

In view of subsequently obtained data, it was surprising that 7m8oGuo exhibited enhanced activity over compounds such as 8-hydroxyguanosine (referred to as its tautomer, 8-oxoguanosine; 8oGuo), or 8-mercaptoguanosine (referred to as 8MGuo, or as its tautomer 8-thioxoguanosine). More specifically, subsequent data, some of which are provided hereinafter, revealed that the activity (both mitogenicity and adjuvanticity) of a series of 8-substituted guanosines decreased with increasing size of the 8-substituent group.

Thus, since the methyl group of 7m8oGuo is bonded on the guanosine ring adjacent to the 8-position where a substituent size effect was found, the addition of that group or any group at the 7-position where there previously was no substituent would have been expected to also cause a decrease in activity merely because the molecule in question was larger at a position adjacent to the size-sensitive ring position. The enhanced adjuvanticity of compounds of the present invention having still larger substituents at the 7-position on the guanosine ring over 7m8oGuo was still more surprising.

II. The Compounds

The immunostimulating compounds contemplated herein are 7,8-disubstituted guanine nucleoside derivatives (also referred to herein as guanosines or guanosine derivatives). These compounds have structures that correspond to formula I shown below:

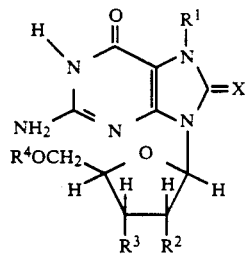

wherein X is O, S, Se or NCN;

$R^1$ is a heteroatom-substituted hydrocarbyl radical having a total length greater than an ethyl group and less than a decyl group and being free from an ionic charge at physiological pH values;

$R^2$ and $R^3$ are the same or different radicals selected from the group consisting of hydrogen, hydroxyl, lower alkoxy, lower alkanoyloxy and benzoxy, or $R^2$ and $R^3$ together constitute a lower alkylidenedioxy radical; and $R^4$ is a radical selected from the group consisting of hydrogen, lower alkanoyl and benzoyl.

It is noted that the ribosyl group in the formula above is intended to be shown bonded at the 1-position of that ring with the bond being in the beta-configuration. In addition, the D form of the ribosyl group is to be understood as intended.

Preferred guanosine derivatives are those in which X is O or S, $R^1$ has a length greater than ethyl and less than about heptyl, and $R^2$ and $R^3$ are other than lower alkylidenedioxy. In particularly preferred practice, X is O, $R^1$ is selected from the group consisting of 2-chloroethyl (—CH$_2$CH$_2$Cl), carbethoxymethyl (—CH$_2$CO$_2$C$_2$H$_5$), carbamoylmethyl (—CH$_2$CONH$_2$), methoxyethyl (—CH$_2$CH$_2$OCH$_3$), 4-nitrobenzyl, 4-methoxybenzyl, and 2,3-dihydroxypropyl, $R^2$ and $R^3$ are hydroxyl, and $R^4$ is hydrogen. Most preferably, X is O, $R^1$ is 4-nitrobenzyl or 2-chloroethyl, $R^2$ and $R^3$ are hydroxyl and $R^4$ is hydrogen.

As noted previously, an $R^1$ radical has a length greater than that of an ethyl group and thus includes heteroatom-substituted ethyl groups where the substituent has a size greater than that of a hydrogen atom. An $R_1$ radical also has a length that is less than that of a decyl group. That is to say that $R^1$ is a heteroatom-substituted hydrocarbyl radical having a length of the longest chain including the substituent that is greater than that of a saturated two carbon chain, and shorter than that of a saturated ten carbon chain; each length including appropriate hydrogen atoms. A heteroatom-substituted hydrocarbyl group referred to simply as a heteroatom-substituted propyl, butyl, hexyl or decyl or the like is to be understood to have a normal, straight chain hydrocarbyl radical. Heteroatom-substituted branch chain radicals are indicated by usually used numerical or abbreviated prefixes such as 2-propyl or iso-propyl, respectively.

Heteroatom-substituted-hydrocarbyl radical chain lengths are measured along the longest chain in the substituent. That longest chain may or may not include the heteroatom-substituent group. These lengths can be readily calculated by using published bond angles, bond lengths and atomic radii, as needed, to draw and measure lengths of staggered chain forms the radicals, or by building models using commercially available kits whose bond angles, lengths and atomic radii are in accord with accepted, published values. In addition, approximate substituent lengths, can be estimated by assuming, unsaturated bond lengths, bond angles and atomic radii as well as those of the atoms of a heteroatom-substituent to be identical to those of saturated carbon atoms, although the above-mentioned modes of measurement are preferred.

$R^1$ is a heteroatom-substituted-hydrocarbyl radical having a particular length that is free from a group that provides an ionic charge at physiological pH values. Thus, the 7-heteroatom-substituted radical is free from amine, carboxylic base or other basic or acetic groups whose pka values are such that the molecule would bear an ionic charge at physiological pH values.

Hydrocarbons and hydrocarbyl radicals can themselves broadly be divided into aliphatic and aromatic radicals. Useful aliphatic radicals include (i) saturated alkane (alkyl radicals) and (ii) mono-unsaturated alkenes and alkynes (alkenyl and alkynyl radicals), respectively. Cyclic, straight chain and branch chain radicals exist for each type of aliphatic radical. Useful aromatic radicals are aralkane radicals that contain an aromatic ring linked to an aliphatic group. Each of those hydrocarbyl radicals is further substituted with a heteroatom (non-carbon or hydrogen atom) in a contemplated $R^1$ radical.

$R^1$ radicals have a length greater than that of an ethyl group and a length shorter than that of a decyl group. Where the $R^1$ radical is a heteroatom-substituted alkyl radical, those alkyl radicals can therefore be referred to as a heteroatom-substituted lower alkyl radicals. The heteroatom-substituted $C_2$–$C_8$ alkyl radicals include several members of the class referred to herein as "lower alkyl" radicals that are useful in heteroatom-substituted alkyl radicals as is discussed hereinafter. Thus, it is appropriate at this place to discuss lower alkyl radicals.

Groups and radicals referred to herein as "lower" denote that they contain 1 to about 6 carbon atoms, and preferably contain 1 to about 3 carbon atoms. This definition applies to the use of the word "lower" as it is used in all of $R^1$, $R^2$, $R^3$ and $R^4$.

Lower alkyl radicals include, for example, methyl, ethyl, propyl, iso-propyl, n-butyl, sec-butyl, t-butyl, n-pentyl, 3-methyl-2-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, and the like. The group of heteroatom-substituted $C_2$–$C_8$ alkyl radicals of $R^1$ includes appropriately heteroatom-substituted methyl radicals of the group of lower alkyl radicals, and further includes heteroatom-substituted heptyl, octyl and nonyl radicals as well as further radicals such as heteroatom-substituted 2-methylheptyl radical that are heteroatom-substituted alkyl substituted lower alkyl radicals. Inasmuch as more preferred $R^1$ radicals have a length greater than ethyl and less than about heptyl, more preferred lower alkyl radicals for $R^1$ include appropriately heteroatom-substituted methyl, as well as substituted propyl, butyl, pentyl, 1-methylbutyl, 2-methylbutyl and the like.

Substituted alkyl $R^1$ radicals include halo-substituted $C_2$–$C_8$ alkyl, hydroxy- and polyhydroxy $C_2$–$C_6$ alkyl, $C_2$–$C_6$ alkylene lower alkyl carboxylate, di-lower alkyl ether (lower alkoxy lower alkyl), and lower alkoxy $C_1$–$C_7$ alkyl carbonyl radicals unsubstituted, as well as mono- and di-lower alkyl lower alkyl carboxamido radicals in which the carboxamido group portion of the radical has the formula $CONR^5R^6$. These $R^1$ radicals are discussed below.

Hydroxy $C_2$–$C_6$ alkyl radicals include 2-hydroxyethyl, 2-hydroxypropyl, 3-hydroxypropyl, 3-hydroxy-2-butyl, 3-hydroxy-2,2-dimethylpropyl, 6-hydroxyhexyl and the like.

Another group of substituted alkyl $R^1$ radicals is a subgroup of hydroxy $C_2$–$C_6$ alkyl radicals that are $C_3$–$C_6$ radicals that contain a hydroxy group spaced two carbon atoms from a further substituent that is selected from the group consisting of azido, ether and thioether substituents wherein the ether and thioether groups contain up to about three carbon atoms. This subgroup can be viewed as the reaction product of an epoxide and a nucleophile. The hydroxy group formed from the epoxide and the nucleophile is most preferably bonded to a three carbon chain such as is provided by the reaction of epichlorohydrin or epibromohydrin with an appropriate guanosine followed by reaction of the resulting epoxide with the nucleophile.

Polyhydroxy $C_3$–$C_6$ alkyl radicals include 2,3-dihydroxypropyl, 3,4-dihydroxybutyl, sorbityl and the like. Those skilled in the art will understand that the contemplated polyols contain no more than one hydroxyl group on each carbon atom of the lower alkyl group.

Halo-substituted $C_2$–$C_8$ alkyl radicals preferably include one or more chlorine, bromine fluorine or iodine atoms bonded to a $C_2$–$C_8$ alkyl radical. Exemplary halo-substituted radicals include 2-chloroethyl, 2,2,2-trifluoroethyl, 2-bromobutyl, 2-chlorohexyl, 2,3-dichlorooctyl, perhalosubstituted-hydrocarbyl and the like.

Lower alkyl carboxy radicals include the before-described lower alkyl radicals that further include a carboxy group ($-CO_2H$) as a substituent.

Thus, a 7-$CH_2CO_2H$ radical is considered to be a carboxy-substituted methyl radical. Lower alkyl carboxy radicals are not themselves contemplated as $R^1$ substituents, as they provide an ionic charge to the guanine derivative at physiologic pH values. However, ester and amide derivatives of lower alkyl carboxy radicals are contemplated.

Lower alkoxy lower alkyl carbonyl radicals can be viewed as esters of lower alkyl carboxy radicals with lower alkyl alcohols such as methyl, ethyl, iso-propyl t-butyl and neo-pentyl alcohols. Exemplary lower alkyl carboxy radicals include carboxymethyl, 2-carboxyethyl, 2-carboxyhexyl and the like. Exemplary lower alkoxy lower alkyl carbonyl radicals include carbethoxymethyl (also known as carboethoxymethyl), 3-isopropoxycarbonylpropyl, 4-hexyloxycarbonylpentyl, and the like.

Unsubstituted, mono- and di-lower alkyl substituted amino lower alkyl carbonyl (lower alkyl carboxamido in which the carboxamido group portion of the radical has a formula $CONR^5R^6$) radicals can be viewed as being formed from a 7-substituent lower alkyl carboxy group and ammonia, as well as mono-lower alkyl or $C_2$–$C_3$ alkanol amine or di-lower alkyl or di-$C_2$–$C_3$ alkanol amine, respectively, where the lower alkyl radicals are as before described, and the $C_2$–$C_3$ alkanol portions are 2-hydroxyethyl, 3-hydroxypropyl or 2-hydroxypropyl. Exemplary of such amines are methylamine, propylamine, sec-butylamine, hexylamine, dimethylamine, methylethylamine, butylhexylamine, 2-hydroxyethylamine (ethanolamine), 2-hydroxypropylamine (isopropanolamine), diethanolamine, diisopropanolamine, methylethanolamine, 3-propanolamine and the like. Amides of cyclic secondary amines having five or six atoms in the ring can be viewed as being formed from a lower alkyl carboxy group and a cyclic secondary amine such as pyrrolidine, morpholine, piperidine, pyrrole or 4-methylpiperazine.

The carboxamido group portion of a lower alkyl carboxamido radical such as those above has the formula $CONR^5R^6$ wherein $R^5$ and $R^6$ are the same or different and are selected from the group consisting of hydrogen, lower alkyl and $C_2$–$C_3$ alkanol. Alternatively, $NR^5R^6$ together can form a heterocyclic ring having five or six atoms in the ring. Thus, these 7-substituents can be described as lower alkyl carboxamido radicals whose carboxamido group portion has the formula $CONR^5R^6$.

A $C_2$–$C_6$ alkylene lower alkyl carboxylate radical can be viewed as an ester of a substituent hydroxy $C_2$–$C_6$ alkyl or polyhydroxy $C_3$–$C_6$ alkyl radical and a lower alkyl carboxylic acid. Exemplary hydroxy $C_2$–$C_6$ alkyl substituents have been discussed previously. Lower alkanoyl (lower acyl) portions of lower alkyl carboxylic acids that can be present in such esters include formyl, acetyl, propionyl, 2-methylpropionyl, butyryl, 3-methylvaleryl and the like. Lower alkanoyloxy groups formed by the esterification of a 2'-and/or 3'-hydroxyl group and a lower alkyl carboxylic acid such as those above are contemplated as $R^2$ and $R^3$. Lower alkanoyl groups similarly formed by esterification of a 5'-hydroxyl group are contemplated as $R^4$ radicals.

A $C_2$–$C_6$ alkylene lower alkyl carboxamide radical is also contemplated as a heteroatom-substituted 7-hydrocarbyl substituent. Such a radical can be viewed as an amide formed from a primary or secondary amino-substituted $C_2$–$C_6$ alkyl radical and a lower alkyl carboxylic acid. Primary and secondary amino-substituted $C_2$–$C_6$ alkyl radicals (as well as similarly substituted tertiary amines) are also not themselves contemplated herein as their amino groups provide an ionic charge to the guanine derivative at physiological pH values. Useful lower alkyl carboxylic acids present in such amides are those discussed previously. Exemplary primary and secondary amine substituted $C_2$–$C_6$ alkyl radicals include 2-aminoethyl, 2-aminopropyl, 2-(iso-propyl)aminoethyl (3-aza-4-methylpentyl) radicals, and the like.

It is noted that an ester or amide as described in the preceding paragraphs could theoretically have a length greater than that of a decyl group. However, as noted earlier, an $R^1$ radical has a length that is less than that of a decyl group. Thus, an ester formed from an alkyl carboxylate having six carbons and a lower alkyl alcohol having six carbons is excluded as it is longer than a decyl group. It is also noted that preferred $R^1$ radicals have a length that is less than about that of a heptyl group, and that preference holds for the before-described esters and amides.

Still another group of substituted 7-hydrocarbyl substituents are di-lower alkyl ether radicals, which can also be named as lower alkoxy lower alkyl radicals. Such di-lower alkyl ethers can be considered to be alkyl groups in which one or more methylene groups (—$CH_2$—) are substituted by an oxygen atom (—O—). Exemplary useful ether radicals include methoxymethyl, methoxyethyl, ethoxyethyl, ethoxy-2-propyl radicals and the like.

The previous discussion has dealt with 7-substituents that are heteroatom-substituted straight and branch chain alkyl (aliphatic) radicals. The compounds of the present invention also include substituted cyclo aliphatic, ethylenically unsaturated aliphatic and aralkyl radicals. Each of those radicals can be heteroatom-substituted as has been discussed for the straight and branch chain alkyl radicals.

For example, heteroatom-substituted cyclic aliphatic radicals such as cyclopentanecarboxylic acid or cyclobutanecarboxylic acid can be utilized to form an ester or amide with a previously mentioned 7-substituted lower alkyl alcohol or amine, respectively. The same is the case for ethylenically unsaturated cyclic carboxylic acids such as 2-cyclopentene-1-acetic acid. Similarly, a cyclic alcohol such as cyclohexanol or 2-cyclohexen-1-ol, cyclopropyl carbinol, or a cyclic amine such as cyclobutylamine or cyclohexylamine can be utilized to form an ester or amide, respectively, with a previously-discussed 7-alkylcarboxy radical such as a carboxymethyl radical. Ethylenically unsaturated alcohols and carboxylic acids such as 3-butyn-1-ol, and 3,3-dimethylacrylic acid can also be used in the preparation of esters and amides as discussed before.

Substituted aralkyl radicals are particularly contemplated $R^1$ radicals. Exemplary aralkyl radicals include benzyl and phenethyl radicals, and those radicals are substituted on their phenyl rings with one or two, preferably one, heteroatom-substitutent selected from the group consisting of nitro, cyano, carboxamido (—$CONR^5R^6$, wherein $R^5$ and $R^6$ are as before described), halogen, lower alkoxy, lower alkoxy carbonyl, hydroxyl and lower alkanoyloxy groups. It is reiterated that the total length requirement for the $R^1$ radical is maintained.

Substituents on a benzyl group that are electron withdrawing groups relative to hydrogen by resonance or inductive effect as are discussed in Hine, *Physical Organic Chemistry*, 2nd ed., McGraw-Hill Book Co,. New York, pages 85–93 (1962) such as cyano, nitro and halogen are preferred. A 4-nitrobenzyl radical is a particularly preferred radical, as is 7-(4-nitrobenyl)-8-oxoguanosine a particularly preferred guanine derivative of the invention.

Of the above heteroatom-substituted-hydrocarbyl radicals, substituted straight chain alkyl and benzyl hydrocarbyl radicals having a length greater than ethyl and less than about heptyl are preferred. Of that preferred group, halo-substituted alkyl, lower alkyl lower alkyl carbonyl, lower alkyl carboxamido in which the carboxamindo portion has the formula $CONR^5R^6$, lower alkoxy lower alkyl, and benzyl whose phenyl ring is substituted with an electron withdrawing group relative to hydrogen are particularly preferred radicals.

$R^2$ and $R^3$ radicals can be the same or different, and are selected from the group consisting of hydrogen, hydroxyl, lower alkoxy, lower alkanoyloxy and benzoxy. $R^2$ and $R^3$ together can also form a 2',3'-cyclic lower alkylidenedioxy radical. Exemplary $R^2$ and $R^3$ radicals are discussed below.

Lower alkoxy radicals are lower alkyl radicals bonded to the guanine sugar (ribose) ring through an oxygen atom of the sugar. Exemplary lower alkoxy radicals include methoxy, ethoxy, iso-propoxy, butoxy, hexyloxy and the like. Lower alkanoyloxy radicals are esters formed between a guanine sugar ring hydroxyl group and a lower alkyl carboxylic acid. Examples of lower alkanoyloxy radicals include formoxy, acetoxy, propionoxy, hexanoyloxy and the like.

Lower alkyl acetal and ketal derivatives of the 2'- and 3'- hydroxyl groups are referred to as 2',3'-cyclic lower alkylidenedioxy or more simply as lower alkylidenedioxy radicals. These radicals are formed by reaction of an aldehyde such as formaldehyde, acetaldehyde or the like, or a ketone such as acetone or methylethyl ketone with the 2'- and 3'-hydroxyl groups of a substituted guanosine ribosyl group.

It is preferred that $R^2$ and $R^3$ be hydroxyl, lower alkanoyloxy or benzoxy, and more preferably hydroxyl or acetoxy. When $R^2$ and $R^3$ are lower alkanoyloxy or benzoxy, those radicals may be lost during or soon after the leukocyte contacting step of a method of the invention, and thus may provide a "pro drug" form of the guanosine derivative. Most preferably, $R^2$ and $R^3$ are hydroxyl.

$R^4$ is a radical selected from the group consisting of hydrogen, lower alkanoyl and benzoyl. $R^4$ is most preferably hydrogen. When $R^4$ is lower alkanoyl or benzoyl, it is also believed that the carboxyl group-containing radical may be cleaved as described above, again providing a "pro drug".

A useful guanosine is substantially free from ionic charge at physiological pH values; i.e., about pH 7.0 to about pH 7.5, except for the ionic charges that might be provided by the relatively acidic 1-position ring nitrogen atom. Thus, a useful molecule is free of acid and base-containing moieties that are not present in guanosine. That freedom from acidic and basic groups extends from the $R^1$ radical, and throughout the whole guanosine molecule.

The guanines are acids, and as such can form base addition salts. Such salts are useful in providing storage stability and do not provide an added ionic charge to a guanine derivative used in a method of the invention because of the buffering effect provided by the host's blood and lymph systems or the buffer of a culture medium.

Pharmaceutically acceptable, non-toxic base addition salts of guanine derivatives are useful herein, and can be formed by treatment of the immune response-enhancing agent with an appropriate base, in a suitable solvent such as water or a lower alkyl alcohol such as methanol or ethanol. Exemplary inorganic bases include sodium hydroxide, potassium hydroxide, ammonium hydroxide and the like. Exemplary organic bases include tris-(hydroxymethyl)-aminomethane (TRIS), 4-(2-hydroxyethyl)-1-piperazine-ethanesulfonic acid (HEPES) and the like bases. Conversely, the base addition salt form can be converted to the free guanosine form by treatment with acid.

The substituted guanine nucleoside derivatives useful herein are readily prepared by procedures published in the chemical literature, or by procedures analogous thereto. Several exemplary syntheses are provided hereinafter in the Materials and Methods Section. Syntheses of 7,8-disubstituted guanine nucleoside derivatives typically begin with the 9-1'-beta-aldoglycoside bond already formed, although the initial formation of that bond is not required.

In addition to the exemplary syntheses described hereinafter, three general synthetic modes are described briefly here. These modes are exemplary of the synthetic modes provided by the literature, and are described using a 7-heteroatom-substituted-hydrocarbyl-8-thioxoguanosine of the invention as the compound to be prepared.

In a first mode, a 7-heteroatom-substituted-hydrocarbyl-8-thioxoguanine is reacted with a suitable alpha-1-leaving group-substituted ribose derivative such as alpha-1-chloro (or bromo or acetoxy)-2,3,5-tribenzyoyl-D-ribose in a suitable solvent to form the beta-ribosyl derivative. The reaction products are collected, and separated by HPLC to obtain the desired guanosine derivative.

In a second mode, 7-allyl-8-thioxoguanosine (22444; Example 20) is oxidized to form the corresponding aldehyde. The resulting 7-(2-ethanal)-8-thioxoguanosine is thereafter condensed via a Wittig, Claisen, Reformatsky or the like reaction to form a an unsaturated 7-heteroatom-substituted guanosine that is separated from other products present for use, or can be reduced or halongenated prior to use.

The 7-(2-ethanal) derivative can also be reductively alkylated to form a lower alkyl amine substituent from which a $C_2$–$C_6$ alkylene lower alkyl caboxamide radical can be formed. Still further, the 7-(2-ethanal)derivative can be reduced to the corresponding 7-(2-ethanol) derivative that is itself useful, and can also be esterified to form a $C_2$–$C_6$ alkylene lower alkyl carboxylate.

In a third mode, ring closure by a reaction of thiophosgene with an appropriately substituted 2,5,6-triamino-4-hydroxypyridmidine is utilized. More specifically, a 2-amino-4-hydroxy-5-heteroatom-substituted-hydrocarbyl-6-beta-D-ribosylpyrimidine is reacted with thiophosgene in the presence of an acid-scavenging base to provide a 7-heteroatom-substituted hydrocarbyl-8-thioxoguanosine derivative that can be separated from other reaction products for use.

III. The Compositions

A composition of this invention comprises a diluent amount of a physiologically tolerable carrier (also referred to herein as a vehicle or diluent) admixed with an immunopotentiating (immune response-enhancing or immunostimulating) effective amount of an substituted guanine nucleoside derivative or salt of this invention described before.

A composition for in vivo administration is typically provided for per oral or parenteral administration in customary unit dosage compositions. The term "unit dosage" and its grammatical equivalents as used herein refer to physically discrete units suitable as unitary dosages for human patients and other mammals, each unit containing a predetermined effective amount of the guanosine active ingredient calculated to produce the desired therapeutic effect in association with the required physiologically tolerable carrier, e.g. a diluent or a vehicle The specifications for the novel unit dosage forms of this invention are dictated by and are directly dependent on (a) the unique characteristics of the active guanosine derivative ingredient and the particular therapeutic effect to be achieved, and (b) the limitations inherent in the art of compounding such an active ingredient for therapeutic use in vitro, as well as in vivo in humans and other animals.

Examples of suitable unit dosage forms in accord with this invention are tablets, capsules, pills, powder packets, granules, wafers, and the like, segregated multiples of any of the foregoing, as well as liquid solutions, emulsions and suspensions. Liquid compositions can be administered in usual manners such as subcutaneously, intraperitoneally, intramuscularly, perorally or the like.

The amount of active ingredient that is administered in vivo as an effective immunostimulating amount depends on the age and weight of the patient, the particular condition to be treated, the frequency of administration, and the route of administration. The total daily dose range can be about 0.01 to about 200 milligrams per kilogram of body weight, more preferably about 0.1 to about 25 milligrams per kilogram of body weight, and most preferably about 1 to about 15 milligrams per kilogram of body weight. The human adult dose is in the range of about 5 to about 1400 milligrams daily, given either as a single dose or in 3 or 4 divided doses. Veterinary dosages correspond to human dosages with the amounts administered being in proportion to the weight and metabolic rate of the animal as compared to adult humans.

It will be appreciated by those skilled in the art that useful in vivo concentrations can vary from animal species to animal species. Those skilled workers also know that appropriate concentrations can be readily determined.

Concentrations for the in vitro contacting of animal cells are about $1 \times 10^{-6}$ molar to about $3 \times 10^{-4}$ molar for cell concentrations of about $10^6 \times 10^7$ cells per milliliter. More preferably, the concentration is about $1 \times 10^{-5}$ molar to about $1 \times 10^{-4}$ molar As will be seen from the Results Section hereinafter, the peak concentration; i.e., the concentration that provides the greatest adjuvanticity, for a given guanosine can vary as ten or more fold when studied in mouse and human lymphocyte systems.

A composition can be a solid or a liquid. Physiologically tolerable carriers are well known in the art. Exemplary of liquid carriers are sterile aqueous solutions that contain no materials in addition to the active ingredient guanosine derivative and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. The latter carriers are exemplified by Ringer's Injection, Dextrose Injection, Dextrose and Sodium Chloride Injection and Lactated Ringer's Injection.

Liquid compositions can also contain liquid phases in addition to and to the exclusion of water. Exemplary of such additional phases are glycerin, vegetable oils, such as cotton seed oil, sesame oil and water-oil emulsions.

Exemplary solid carriers include those materials usually used in the maunufacture of pills or tablets, and include corn starch, lactose, dicalcium phosphate, thickeners such as tragacanth gum and methylcellulose U.S.P., finely divided $SiO_2$ polyvinylpyrrolidone, magnesium stearate and the like. Additionally, the solid carrier can include biodegradable and non-biodegradable polymers, polypeptide carriers, affinity carriers such as AFFI-GEL 601 (phenyl boronate resin available from BIO-RAD Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide aspartic-phenylalanine methyl ester sweetener sold under the tradename NUTRASWEET (aspartame) by G. D. Searle Co.

IV. Method of Immunostimulation

A method of enhancing the immune response of leukocytes is also contemplated. Preferably, the immune response is an antigen-specific response. In accordance with this method, leukocytes such as lymphocyte preparations, B cells, T cells, neutrophils and macrophages are contacted separately or in combination in an aqueous medium with a before-described composition containing an immunostimulating effective amount of a before-described guanine nucleoside derivative.

The method can be practiced in vivo in humans, laboratory mammals such as mice, rats and guinea pigs or in veterinary animals and pets such as pigs, horses, cattle, dogs and cats. The method can also be practiced in vitro in cell cultures such as in hybridoma culture for the production of monoclonal antibodies.

The leukocytes are contacted in an aqueous medium regardless of whether the composition of guanosine derivative is itself a solid or liquid, or whether or not the liquid of the composition is aqueous. For the in vivo method, the aqueous medium is supplied at least in part by the water of the blood or lymph. For in vitro methods, the aqueous medium is supplied at least in part by the culture medium used.

Contact between the composition and leukocytes is maintained for a time period sufficient for the contacted cells to manifest the enhancement of their immune response. That immunostimulation can itself be manifest in cellular proliferation, enhanced antibody secretion, enhanced T helper activity, enhanced cytokine production from T cells and macrophages, enzyme secretion from neutrophils, and the like.

The specific results discussed hereinafter illustrate a non-specific mitogenic responses of murine spleen cells, as well as the preferred antigen-specific responses of murine B cells and human peripheral blood lymphocytes depleted of T suppressor cells. Additional illustrative antigen-specific immunoenhancements that can be achieved using a method of the invention include proliferation of T cells, the in vitro reconstitution of the primary immune response in murine immunodeficient B cells, T cell-replacing activity in murine B cells, and an in vivo enhancement of murine antibody production.

For use in vivo, contact between leukocytes and a composition is typically maintained for a time period sufficient for the animal to clear the guanosine derivative from its body as by metabolism, excretion or both processes. That time period can be longer than that required for immunostimulation to be manifest. Contact with an individual unit dose is typically maintained for a time period of hours to about a week or more, depending, for a given compound, upon the carrier or vehicle used. Continual contact can be advantageous for an immunodeficient animal host.

Contact in vitro can be maintained for a period of time sufficient for one of the before-described immunostimulations to become manifest as determined by standard assay techniques. Such maintenance times typically take about one to about seven days of time, and more usually about 2 to about 6 days.

V. Results

Specific results utilizing the compounds, compositions and methods of this invention have been obtained, and those results have often been compared to similar results obtained using compounds, compositions and methods disclosed in U.S. Pat. No. 4,643,992. Some of the compounds utilized in U.S. Pat. No. 4,643,992 were utilized for comparative purposes herein. Those compounds are 8-mercaptoguanosine, 7-methyl-8-oxoguanosine and 8-bromoguanosine, and they are abbreviated herein as 8MGuo, 7m8oGuo and 8BrGuo, respectively.

The results discussed hereinafter were obtained using one or more compounds of the invention, unless otherwise noted, in a composition of the invention that is used in a method of the invention. For brevity, and ease of description, only the compounds will be referred to hereinafter with the understanding that such compounds are utilized in compositions and methods of the invention.

Each of the new compounds whose activity is discussed or compared herein has also been given an identifying five-digit number. Those numbers are listed in the title of the Example that describes preparation of the compound. The five-digit number and/or the Example number is utilized in the tables and discussion that follow to identify those compounds.

A. Activities of 8-Substituted Guanosines

As noted earlier, the adjuvanticity and mitogenicity of a series of 8-substituted guanosines not of this invention having thioethers of varying lengths was examined. The results of those studies are shown in Tables 1 and 2 below in which horizontal lines across the whole table separate studies from each other.

TABLE 1

Antigen-Specific Adjuvanticity of 8-Thioether guanosines[1]

| Compound[2] | Concentration[3] | Direct Anti-SRBC PFC/Culture[4] | |
|---|---|---|---|
| | | CBA/CaJ | C57BL/6J |
| 22359 | $10^{-4}$ | 123 ± 21 | — |
| (8) | $3 \times 10^{-4}$ | 157 ± 7 | 2620 ± 100 |
| | $10^{-3}$ | 653 ± 52 | 3110 ± 350 |
| 22435 | $10^{-4}$ | 247 ± 38 | — |
| (7) | $3 \times 10^{-4}$ | 582 ± 52 | 913 ± 1110 |
| | $10^{-3}$ | 607 ± 57 | 12,080 ± 470 |
| 8MGuo | $10^{-4}$ | 813 ± 129 | — |
| | $3 \times 10^{-4}$ | 527 ± 25 | 11,000 ± 140 |
| Control | No nucleoside Antigen present | 75 ± 10 | 486 ± 70 |
| 22300 | $10^{-4}$ | 420 ± 105 | — |
| (6) | $3 \times 10^{-4}$ | 870 ± 70 | — |
| | $10^{-3}$ | 490 ± 133 | — |
| 8MGuo | $10^{-4}$ | 813 ± 129 | — |
| | $3 \times 10^{-4}$ | 782 ± 123 | — |
| Control | No nucleoside No antigen | 8 ± 4 | — |
| Control | No nucleoside Antigen present | 307 ± 61 | — |

[1]Adjuvanticities against sheep red blood cells (SRBC) measured in direct plaque-forming cultures per cell culture of lymphocytes from the mouse strains shown. Details of the procedure are provided in the Materials and Methods Section. Standard errors from the enumerated mean values are shown by "± number".
[2]The nucleosides are identified by their five digit numbers and the Example number in which their preparation is shown is within the parenthesis.
[3]Concentration of the nucleoside in moles per liter in the aqueous medium in which the lymphocytes were contacted.
[4]Lymphocytes from inbred mouse lines CBA/CaJ or C57BL6/J were used.

TABLE 2

Mitogenicity of 8-Thioetherguanosines[1]

| Compound[2] | Concentration[3] | [³H]TdR Uptake (cpm/culture) |
|---|---|---|
| 22359 | $10^{-4}$ | 1600 ± 90 |
| (8) | $3 \times 10^{-4}$ | 1300 ± 80 |
| | $10^{-3}$ | 1700 ± 280 |
| 22435 | $10^{-4}$ | 4500 ± 120 |
| (7) | $3 \times 10^{-4}$ | 8800 ± 200 |
| | $10^{-3}$ | 11,200 ± 202 |
| 8MGuo | $10^{-3}$ | 41,100 ± 390 |
| Control | No nucleoside | 2100 ± 60 |
| 22300 | $10^{-4}$ | 2700 ± 130 |
| (6) | $3 \times 10^{-4}$ | 4100 ± 70 |
| | $10^{-3}$ | 16,400 ± 1130 |
| 8MGuo | $10^{-3}$ | 25200 ± 950 |
| Control | No nucleoside | 2400 ± 90 |

[1]Mitogenicity measured by the uptake of [³H]TdR (tritium-labeled thymidine deoxyribonucleoside) using the conditions discussed in the Materials and Methods Section as determined by measuring counts per minute (cpm) per cell culture. Standard deviations are shown as in Table 1.
[2,3]See notes 2 and 3 of Table 1.

The above results illustrate that as the length of the substituent increased, the activity of the 8-substituted guanosine derivative decreased relative to 8MGuo whose 8-sulfur atom was bonded to a hydrogen atom. Thus, the antigen-specific adjuventicity of the 8-(2-butenyl) derivative (22435) was greater than that of the longer 8-cinnamyl derivative (22359), but less than that of the 8-mercapto compound (8MGuo). The 8-allyl derivative (22300) had about equal adjuvanticity to that of 8MGuo for the concentrations shown. The results for mitogenicity for the same compounds showed an even more pronounced trend in activities with increasingly longer 8-substituents providing increasingly poorer results.

B. Adjuvanticity And Mitogenicity Need Not Be Related

The compounds, compositions and methods of the present invention are useful in enhancing mitogenic and polyclonal responses, and adjuvanticity as are the compounds whose activities are illustrated in Tables 1 and 2. The mitogenic and adjuvant properties of the present compounds are thought to result from at least two different pathways in which mitogenesis and a polyclonal response are often coincident results, whereas adjuvanticity results frequently differ. See, for example Goodman et al., *J. Exp. Med.*, 147:800 (1978) and McIntire et al., *J. Immunol.*, 117:674 (1976). Some similar differences are discussed in U.S. Pat. No. 4,643,992.

This uncoupling of activities is also shown for some of the compounds discussed herein as can be seen from the results of Tables 3 and 4, below.

TABLE 3

Antigen-Specific Adjuvanticity of Some 7-Heteroatom-Substituted-hydrocarbyl-8-oxoguanosines in the Human System[1]

| Compound[2] | Concentration[3] | PFC/Culture |
|---|---|---|
| 22935 | $3 \times 10^{-5}$ | 175 ± 33 |
| (2) | $10^{-4}$ | 3613 ± 717 |
| | $3 \times 10^{-4}$ | 13,013 ± 2613 |
| 22943 | $3 \times 10^{-5}$ | 83 ± 12 |
| (4) | $10^{-4}$ | 58 ± 4 |
| | $3 \times 10^{-4}$ | 222 ± 54 |
| Control | No nucleoside No antigen | 0 ± 1 |
| Control | No nucleoside Antigen present | 150 ± 15 |

[1]Studies were carried in a manner similar to those of Table 1, except that a human lymphocyte preparation was used.
[2,3]See notes 2 and 3 of Table 1.

TABLE 4

Mitogenicity of Some 7-Heteroatom-Substituted-8-oxoguanosines in the Human System[1]

| Compound[2] | Concentration[3] | [³H]TdR Uptake (cpm/culture) |
|---|---|---|
| 22935 | $3 \times 10^{-5}$ | 5,975 ± 449 |
| (2) | $10^{-4}$ | 38,505 ± 655 |
|  | $3 \times 10^{-4}$ | 60,217 ± 272 |
|  | $10^{-3}$ | 70,944 ± 453 |
| 22943 | $3 \times 10^{-5}$ | 1,077 ± 40 |
| (4) | $10^{-4}$ | 1,814 ± 71 |
|  | $3 \times 10^{-4}$ | 15,714 ± 856 |
|  | $10^{-3}$ | 77,100 ± 799 |
| Control | No nucleoside | 1508 ± 125 |

[1,2,3] See Notes 1, 2 and 3 of Table 2.

The above results illustrate that 7-(3-dimethylamino)-propyl-8oxoguanosine (22943) was mitogenic in a murine system (Table 4) as compared to 7-carbethoxymethyl-8-oxoguanosine (22935). However, the amine-containing compound (22943) exhibited an activity about equal to that shown by one of the controls (no nucleoside+antigen) when those same compounds were examined for adjuvanticity using human lymphocytes (Table 3).

The above results further confirm that mitogenicity and adjuvanticity are not necessarily linked and can proceed by different pathways. Those results also illustrate the lack of adjuvanticity exhibited by compounds containing otherwise useful structural elements, e.g. the guanosine ring, an 8-oxo group and a 7-heteroatom-substituted hydrocarbyl radical longer than ethyl but shorter than decyl, but that bears an ionic charge at physiological pH values, here due to the dimethylamino group.

It is further noted that although mitogenicity and adjuvanticity can be shown in vitro in the mouse system, only adjuvanticity has been observed in vitro in the human system using any of the compounds discussed herein.

C. Adjuvanticity Studies

A number of comparisons of adjuvanticity to SRBC using human and murine lymphocytes as the source of leukocytes have been carried out using compounds of the present invention, as well as with new compounds excluded from the present invention. Unfortunately, due to the differences in lymphocyte responses even from inbred mice, let alone the outbred human population, these results are very difficult to compare accurately with each other. Rather, they can best be compared within a given study to those compounds used in the study and to the controls for each study. Tables 5 and 6, hereinafter, provide exemplary data from such studies in which only the activity at the peak concentration is shown for each compound. Each study is separated from the others by a horizontal line across the table.

TABLE 5

Adjuvanticity Studies in the Murine System[1]

| Compound[2] | Peak Concentration[3] | Direct anti-SRBC PFC/Culture |
|---|---|---|
| 22935 (2) | $10^{-4}$ | 2371 ± 179 |
| 22943 (4) | $3 \times 10^{-4}$ | 2283 ± 104 |
| 23090 | $10^{-5}$ | 40 ± 3 |
| (5) |  |  |
| Control | No nucleoside No antigen | 33 ± 9 |
| Control | No nucleoside Antigen present | 20 ± 3 |
| 24599 (18) | $3 \times 10^{-5}$ | 2521 ± 191 |
| 8BrGuo | $10^{-3}$ | 2450 ± 325 |
| Control | No nucleoside No antigen | 12 ± 2 |
| Control | No nucleoside Antigen present | 45 ± 10 |
| 7m8oGuo | $3 \times 10^{-5}$ | 1809 ± 39 |
| 24670 (12) | $10^{-4}$ | 1945 ± 191 |
| Control | No nucleoside No antigen | 53 ± 3 |
| Control | No nucleoside Antigen present | 282 ± 46 |
| 24455 (14) | $10^{-4}$ | 230 ± 76 |
| Control | No nucleoside No antigen | 20 ± 5 |
| Control | No nucleoside Antigen present | 203 ± 25 |
| 24331 (10) | $3 \times 10^{-4}$ | 215 ± 5 |
| 24364 (11) | $3 \times 10^{-5}$ | 50 ± 13 |
| Control | No nucleoside No antigen | 8 ± 3 |
| Control | No nucleoside Antigen present | 55 ± 8 |
| 24292 (13) | $10^{-4}$ | 2491 |
| Control | No nucleoside No antigen | 50 |
| Control | No nucleoside Antigen present | 161 |
| 23880 (15) | $10^{-4}$ $10^{-4}$ | 735 ± 56[a] 6408 ± 464[b] |
| Control | No nucleoside No antigen | 17 ± 7[a] 458 ± 13[b] |
| Control | No nucleoside Antigen present | 357 ± 12[a] 1960 ± 120[b] |
| 23756 (16) | $10^{-4}$ | 2376 ± 212 |
| Control | No nucleoside No antigen | 165 ± 40 |
| Control | No nucleoside Antigen present | 305 ± 65 |
| 23642 (3) | $3 \times 10^{-4}$ | 1103 ± 123 |
| Control | No nucleoside No antigen | 72 ± 12 |
| Control | No nucleoside Antigen present | 293 ± 22 |

[1,2] See notes 1 and 2 of Table 1.
[3] The concentration providing the greatest number of plaques per culture in a given study is the value reported.
[a,b] Two studies ("a" and "b") were carried out with the results for studies "a" and "b" being so labeled.

The results in the above Table illustrate several points. First, the compounds of the present invention are generally more active than are the compounds disclosed in U.S. Pat. No. 4,643,992. That improvement in activity was manifest either in a concentration at which peak adjuvanticity was observed (peak concentration) being about 0.5 to one log units (powers of ten) lower, or an adjuvanticity at a given peak concentration that was significantly higher, usually at least about 100 percent higher, than that exhibited for a compound of that patent. The improved adjuvanticity can be seen, for example, where 8BrGuo was compared to 7-(2-chloroethyl)-8-oxoguanosine (24599) in which both compounds had similar numbers of plaques per culture, but the 2-chloroethyl derivative exhibited that value at a concentration 1.5 log units (about 30-fold) lower in concentration.

The above data for 7m8oGuo and the 7-(2-hydroxy-3-azido)propyl derivative (24670) appear to contain at least two anomalies. The peak for 7m8oGuo appeared at an unusually low concentration, and the PFC/culture value appears somewhat elevated from values usually observed The PFC/culture value for compound 24670 also appears somewhat low.

The results in Table 5 also illustrate the unacceptable results obtained with otherwise new and unobvious compounds that are excluded from this invention. Exemplary excluded compounds include 7-[2-(1-piperidino)ethyl]-8-oxoguanosine (23090), 7-[3-(3,4-dimethoxyphenylamino)2-hydroxy]propyl-8-oxoguanosine (24364), 7-[3-(dimethylamino)propyl]-8-oxoguanosine (22943) and 7-carboxymethyl-8-oxoguanosine (23642) that provide an ionic charge to the molecule at physiological pH values.

It is noted that the latter two compounds (22943 and 23642) provided apparently high numbers of plaques in the murine system. However, those relatively high numbers of plaques were provided at concentrations ($3 \times 10^{-4}$ molar) that were relatively too high to be useful, and are presumably due to unionized portions of those molecules also present at equilibrium. In addition, as will be seen from the data of Table 6, compound 22943 was substantially inactive at the same relatively high concentration in the human system.

Attention is also to be drawn to the results for 7-[3-(4-fluorophenyl)piperazinyl-2-hydroxypropyl]-8-oxoguanosine (24455) as well as compound 24364 discussed above. Each of those two compounds was found to be substantially inactive at the concentrations used in the studies. Each also contains a 7-heteroatom-substituted-hydrocarbyl substituent radical that is longer than a decyl group. Those two compounds also contain amine groups that would exhibit an ionic charge at physiological pH values. 7-[2-Hydroxy-3-(phenylthio)propyl]-8-oxoguanosine (24331), whose 7-heteroatom-substituent is slightly longer than octyl, exhibited a relatively small amount of activity.

The results shown in Table 6, below, were obtained similarly to those of Table 5 using human lymphocytes rather than leukocytes from mice.

TABLE 6

| Compound[2] | Adjuvanticity Studies in the Human System[1] | |
|---|---|---|
| | Peak Concentration[3] | Direct anti-SRBC PFC/Culture |
| 22935 (2) | $3 \times 10^{-4}$ | 13,013 ± 2613 |
| 22943 (4) | $3 \times 10^{-4}$ | 222 ± 54 |
| Control | No nucleoside No antigen | 0 ± 0 |
| Control | No nucleoside Antigen present | 150 ± 15 |
| 23756 (16) | $10^{-4}$ | 25,083 ± 546 |
| 23890 (17) | $10^{-4}$ | 15,583 ± 435 |
| Control | No nucleoside No antigen | 2 ± 2 |
| Control | No nucleoside Antigen present | 398 ± 52 |

TABLE 6-continued

| Compound[2] | Adjuvanticity Studies in the Human System[1] | |
|---|---|---|
| | Peak Concentration[3] | Direct anti-SRBC PFC/Culture |
| 7m8oGuo | $3 \times 10^{-4}$ | 5775 ± 214[a] |
| | $10^{-3}$ | 830 ± 67[b] |
| | $10^{-3}$ | 1225 ± 175[c] |
| Control | No nucleoside No antigen | 12 ± 4[a] |
| | | —[b] |
| | | —[c] |
| Control | No nucleoside Antigen present | 652 ± 86[a] |
| | | 82 ± 9[b] |
| | | 143 ± 175[c] |

[1,2,3]See notes 1, 2 and 3 of Table 5.
[a,b,c]Exemplary results from three studies using 7m8oGuo with lymphocyte preparations from three persons designated a, b and c. Compound comparisons are therefore made within a given lymphocyte preparation. The results labeled "a" are to be compared with themselves, as are those labeled "b" and those labeled "c".

The results in Table 6 again show the enhanced efficacy of compounds of the present invention as compared indirectly with 7-methyl-8-oxoguanosine in the human system. Those results again show that a compound providing an ionic charge at physiological pH values, e.g., 7-(3-dimethylamino)propyl-8-oxoguanosine (22943), to be substantially inactive compared to the other compound of the invention.

The indirect but great enhancement of advanticity of compounds of the invention [22935, 23756 and 23890] over 7m8oGuo in the human system both as to the magnitude of the response and the lessened dosage required to produce that response further illustrates the efficacy of using 7-heteroatom-substituted-hydrocarbyl substituents whose substituent length is greater than ethyl but less than decyl.

Still another unexpected property of the more preferred compounds; i.e., where $R^1$ is longer than ethyl and shorter than decyl and where the ribosyl group is unsubstituted, is that the dose-response curve is broader near the peak concentration than is a similar curve obtained for m8oGuo. This broadened response is not seen from the single-valued Tables above.

A measure of relative breadth can be obtained by summing the average number of plaques (PFC/culture) found at a concentration one-half log unit from the concentration that produced the peak value and the PFC/culture at the peak concentration. The sum so obtained is then divided by two (the number of values summed) to provide the average ½ log plaque value.

More specifically, individual average plaque values are selected, and the background value where SRBC alone were present is substracted from each value prior to its being summed, to provide "net" values. Each net value is divided by the number of micromoles of nucleoside present in the 1 ml culture (molar concentration/$10^{-3}$) to provide PFC/culture/micromole. The two greatest values so obtained that include the peak concentration value and an adjacent ½ log unit value are selected, summed and divided by two to yield the average ½ log per micromole value.

When calculations such as those above are carried out for the otherwise unrelated studies of Table 6, one finds that the average ½ log plaque per micromole values for the compounds of the invention are much greater than is the value for 7m8oGuo. Values so calculated are shown in Table 7, below. Similar results are obtained in the murine system.

TABLE 7

Average ½ Log Plaque Values[1]
In the Human System

| Compound[2] | Value |
| --- | --- |
| 7m8oGuo | 21,604[a] |
|  | 787[b] |
|  | 1300[c] |
| 23756 | 158,108 |
| (16) |  |
| 23890 | 85,818 |
| (17) |  |
| 22935 | 38,753 |
| (2) |  |

[1] Values were obtained as described above using data that under lay the results shown in Table 6.
[2] See note 2 of Table 1.
[a,b,c] See Table 6.

Although the results shown in Table 7 are not directly comparable since they were obtained from separate studies, the differences in calculated values are so great that they are believed to be significant.

A dose response curve can be too narrow and thereby not permit appropriate dosing of a particular recipient. For example, the data for the human system shown in Table 6 illustrate differences of as much as a factor of three to ten (one-half to one log unit) in the peak concentration of the compounds studied when lymphocyte preparations from different individuals were compared. If the dose-response curve were too narrow, a selected dosage usual for recipients generally could be too high or too low for a particular recipient. Thus, the broadened dose-response curves for the preferred compounds offer a further advantage compared to 7m8oGuo.

D. T Cell-Replacing Activity

A composition of this invention can be used to substitute for T cells in the antibody response to a T-dependent antigen. Here, murine B cells generated in vitro by treatment with monoclonal anti-thy 1.2 plus complement are cultured with or without SRBC as antigen in the presence of compositions containing incremental concentrations of a 7-heteroatom-substituted-hydrocarbyl substituent guanosine derivative.

Under these conditions, isolated B cell cultures respond poorly to antigen unless supplemented with a guanosine derivative of the invention. The guanosine-modulated response is dose-dependent as well as antigen-dependent. Thus, contacting B cells in vitro with a composition of this invention provides a T cell-like signal to those contacted cells.

E. In Vitro Reconstitution of the Primary Humoral Immune Response

CBA/N mice possess an x-chromosome linked (x-linked) primary B cell immunodeficiency, and thereby can provide a murine model for sex-linked immunodeficiency. The CBA/N strain is thought to be deficient in the functional activity of a subpopulation of mature B lymphocyts bearing the Lyb 3/5/7 antigens. See, Huber et al., *J. Exp. Med.*, 145:1(1977); Ahmed et al., *J. Exp. Med.*, 145:101 (1977); and Subbaro, *J. Immunol.*, 122:2279 (1979).

Cultures of spleen cells from male and female homozygous CBA/N mice and male mice heterozygous for the CBA/N gene, called the xid gene, (male mice bear the x chromosome) is prepared as described in the Materials and Methods section. 0.1 Milliters of a 0.1 percent (v/v) SRBC suspension alone or the SRBC suspension plus incremental amounts of a guanosine of the invention are added to the cultures, using $5 \times 10^6$ cells/ml. Direct anti-SRBC plaque-forming cultures per culture are assessed after 4 days of culture.

Using a similar preparation of spleen cells from immunocompetent CBA/CaJ mice shows that at the zero guanosine derivative concentration level there is substantially no response for the CBA/N cells, as compared to a positive PFC/culture response for the immunocompetent CBA/CaJ cells.

At concentrations of about $10^{-4}-10^{-5}$ molar guanosine derivative, both the immunocompetent CBA/CaJ cells and originally immunoincompetent CBA/N cells are made capable of producing significant numbers of PFC/culture. Thus, contacting x-linked immunodeficient splenocytes with a composition of this invention can reconstitute the primary humoral immune response to SRBC of those otherwise immunodeficient cells.

Immunodeficiency in mice as well as other mammals can come from old age or senescence as well as by genetic defect as discussed above. Thus, animals that were immunocompetent as juveniles or adults can become immunodeficient as they reach old age. That is the case for the inbred CBA/CaJ mouse strain.

A further study of the reconstitution of a primary humoral antibody response to SRBC is carried out using spleen cells from senescent, 156-week old, CBA/CaJ mice that have become immunodeficient through age. The in vitro responses of those spleen cells to SRBC in a plaque-forming assay are compared to similar responses from cells of another group of healthy, adult 8-week old, CBA/CaJ mice. This comparison is carried out as described above, again using a composition containing a guanosine of the invention to contact the splenocytes.

The PFC/culture for the healthy, adult mice controls containing SRBC but no guanosine derivative are several times the number formed in the absence of both SRBC and guanosine. The PFC/culture for the controls for the senescent mice are about equal for both controls, and elevated compared to those of healthy adults. Those relatively elevated and similar responses are thought to be due to the formation of autoantibody-producing clones.

A guanosine derivative dose-related response to SRBC is observed. That response is observed for both the immunocompetent healthy adult splenocytes and the previously immunodeficient, but now primary humoral response-reconstituted senescent splenocytes. Such results thereby illustrate that contacting immunodeficient senescent splenocytes with a composition of this invention can reconstitute this deficient immune response.

F. In Vivo Antibody Responses

CBA/CaJ mice are immunized intraperitonally (i.p.) using a conjugate (TNP-BSA) prepared by the reaction of 2,4,6-trinitrobenzene sulfonic acid (TNBS) and bovine serum albumin (BSA) in a 0.28 molar cacodylate buffer, at pH 6.9. Each animal receives an intraperitoneal (i.p.) injection containing 50 micrograms (ug) of the immunizing conjugate. One group of mice thereafter (within about 30 minutes) receives another i.p. injection that contains a guanosine derivative of the invention in either 100 percent sesame seed oil or an aqueous composition containing 2 volume percent sesame oil sonicated with saline. Each animal receives 0.2 ml of the guanosine derivative from the compositions each of whose concentration of guanosine derivative is 5 mg/ml. A third group of mice receives the immunization but no composition of this invention and serve as a control. Anti-TNP-BSA antibody secretion from each group is thereafter monitored over a period of about 30 days using standard enzyme-linked immunosorbant assay (ELISA) techniques using TNP-BSA as antigen.

The results of such a study indicate that animals receiving a guanosine derivative of the invention exhibit enhanced anti-TNP-BSA antibody titers as compared to titers from animals that do not receive the guanosine derivative.

Having generally described this invention, a further understanding can be obtained by reference to syntheses and procedures that are provided hereinafter below for purposes of illustration.

VIII. Materials and Methods

A. Syntheses

Example 1

General Procedure for Preparation of 7-heteroatom-substituted-hydrocarbyl-8-oxo guanosines 1-Amino-8-oxoguanosine (hereinafter Compound A) served as a starting material for several syntheses using a two-step procedure. That material was prepared essentially by the method described in Rizkalla et al., *Biochim. Biophys. Acta.*, 195: 285–293 (1969).

Step 1

To a solution of Compound A [9.5 grams (g), 30 millimoles (mM)] in dimethyl formamide (DMF) was added sodium methoxide (33 mM) in 250 milliliters (ml) of DMF. The reaction mixture was stirred at ambient temperature (about 18°–22° C.) for 30 minutes. A DMF solution (10 ml), containing the alkylating agent used to form the 7-substituent in a slight molar excess over Compound A (e.g., 33 mM vs. 30 mM) was added, and the resulting alkylating reaction mixture was stirred for a time period of about 16 hours at a temperature of about 20 to about 40 degrees C.

The solvent was thereafter removed in vacuo and the residue treated with distilled or deionized water (150 ml) and methylene chloride (150 ml). The solid obtained was filtered and recrystallized from an appropriate solvent to yield a 1-amino-7-substituted-8-oxo-guanosine, and complete "Step 1" of the usually used two-step synthesis procedure.

Step 2

The product of Step 1 was thereafter dissolved in concentrated HCl (e.g., 4.65 mM in 15 ml of HCl) to which aqueous sodium nitrite was added (e.g. 4.19 mM in 5 ml water) at zero degrees C, followed by stirring for about one hour. The resulting deaminated product was thereafter obtained by standard crystallization techniques unless otherwise noted.

The preparation of specific, exemplary compounds using the above two-step method and other methods are disclosed below, as are other syntheses.

Example 2

7-Carbethoxymethyl-8-oxoguanosine (22935)

The title compound was prepared following the 2 step procedure of Example 1 in which ethyl bromoacetate was used as the step 1 alkylating agent, and was obtained in a 10 percent yield from the corresponding 1-amino compound as a white powder, mp 167°–172° C. NMR (DMSO-d): 10.9 (bs, 1H); 6.5 (bs, 2H); 5.6 (d, J=5Hz, 1H). IR (KBr): 1680, 1620, and 1420 cm$^{-1}$.

| Analysis calculated for $C_{14}H_{19}N_5O_8 \cdot H_2O$: | | |
|---|---|---|
| C, 42.64; | H, 5.11; | N, 17.76 |
| Found: C, 42.44; | H, 4.71; | N, 17.73. |

Replacement of ethyl bromoacetate with 2-chloroacetamide or a N-hydrocarbyl- or N-alkanol-substituted 2-chloroacetamide in the above reaction provides the corresponding 7-carboxamidomethyl-8-oxoguanosine (or corresponding substituted amide, whose carboxamido group has the formula $CONR^5R^6$, wherein $R^5$ and $R^6$ are before-described.) Similarly, replacement of ethyl bromoacetate by a suitable halo ether such as 2-bromoethyl methyl ether or 2-bromoethyl phenyl ether (beta-bromophenetole) provides the corresponding 7-methoxyethyl and phenoxyethyl derivatives, respectively.

Example 3

7-carboxymethyl-8-oxoguanosine (23642)

A mixture of 7-carbethoxymethyl-8-oxoguanosine (1 g, 2.6 mM; Example 2), methanol (5 ml) and 1N NaOH (5 ml) was stirred at room temperature under $N_2$ for 4 hours. Most of the methanol was removed in vacuo, and the residue was heated with water (50 ml). The solution was acidified with 1N HCl at zero degrees C to pH 5. The reaction product was purified by preparative reverse phase high performance liquid chromatography on a C-18 column (HPLC) to give the title compound as a white powder in 31 percent yield, mp above 230° C. NMR (DMSO—d$_6$): δ10.9 (bs, 1H); 6.5 (bs, 2H) 5.6 (d, J=5Hz, 1H); 4.4 (bs, 2H). IR (KBr): 1640, 1600 and 1460 cm$^{-1}$.

| Analysis calculated for $C_{12}H_{15}N_5O_8$ | | |
|---|---|---|
| C, 40.34; | H, 4.23; | N, 19.60 |
| Found: C, 35.71; | H, 3.52; | N, 17.37. |

Example 4

7-[3-(Dimethylamino)propyl]-8-oxoguanosine Monohydrochloride Dihydrate (22943)

Following the two-step procedure of Example 1 in which 3-N,N-dimethylaminopropyl chloride hydrochloride was used as the alkylating agent, potassium carbonate was used as the base, and the deaminated product was treated with one equivalent of HCl in 2-propanol. The title compound was recovered in a 40 percent yield from the 1-amino compound as a white powder; mp 180° C. (decomp.). NMR (DMSO—d$_6$): δ 2.7(s,6H); 5.57 (d,J=5Hz, 1H); 6.91 (bs, 2H); 10.70 (bs, 1H); 11.31 (bs, 1H). IR (KBr): 1670, 1625 and 1590 cm$^{-1}$.

| Analysis calculated for $C_{15}H_{24}N_6O_6$—HCl—$2H_2O$: | | |
|---|---|---|
| C, 39.43; | H, 6.40; | N, 18.40 |
| Found: C, 39.31; | H, 6.15; | N, 18.07. |

Example 5

7-[2-(Piperidino)ethyl]-8-oxoguanosine Monohydrochloride Monohydrate (23090)

Following the procedure of Example 4, but using 2-piperidinoethyl chloride as the alkylating agent, the title compound was obtained in a 34 percent yield from the 1-amino compound as a pale yellow powder, mp 157° C. (decomp.). NMR (DMSO-d$_6$): δ6.65 (bs, 2H); 9.97 (br, 1H); 11.22 (bs, 1H). IR (KBr): 1700, 1670, 1620 and 1590 cm$^{-1}$.

| Analysis calculated for C$_{17}$H$_{26}$N$_6$O$_6$—HCl—H$_2$O: | | |
| --- | --- | --- |
| C, 43.92; | H, 6.29; | N, 18.08 |
| Found: C, 43.99; | H, 6.39; | N, 17.93. |

Example 6

8-(2-Propenylmercapto)guanosine (22300)

Allyl bromide (8g, 63.5 mM) was added to a mixture of 8-thioxoguanosine (8MGuo; 20 g, 63.5 mM) and potassium carbonate (10 g, 72 mM) in dimethyl formamide (DMF) (300 ml), and the resulting mixture was heated with stirring at a temperature of 45° C. for 90 minutes.

The mixture was thereafter cooled to ambient room temperature and poured into a solution of diethyl ether (1.4 l) and acetic acid (5 ml). The resulting solid was filtered and washed with water (250 ml), acetone (200 ml) and then diethyl ether, and thereafter dried in an oven at 60° C. to provide the titled thioether (14.7 g, 67 percent yield) as a white powder, mp 225° C. (decomp.). NMR (DMSO-d ): δ5.70-5.91 (m, 2H); 6.38 (bs, 2H). IR (KBr): 1700, 1640 and 1610 cm$^{-1}$.

| Analysis calculated for C$_{13}$H$_{17}$N$_5$O$_5$S: | | |
| --- | --- | --- |
| C, 43.93; | H, 4.82; | N, 19.71 |
| Found: C, 44.10; | H, 4.82; | N, 19.69. |

Example 7

8-(2-Butenylmercapto)guanosine (22435)

Following the above procedure for the preparation of 8-(2-propenylmercapto)guanosine (Example 6), but substituting 2-butenyl chloride for allyl bromide, the title compound was obtained in 48 percent yield as a white powder, mp 210° C. (decomp.). NMR (DMSO-d$_6$): δ6.3 (bs, 2H); 5.6 (d, J=5Hz, 1H); 1.6 (d, J=6Hz, 3H). IR (KBr): 1690, 1630, 1600, 1510 and 1365 cm$^{-1}$.

| Analysis calculated for C$_{14}$H$_{19}$N$_5$O$_5$S: | | |
| --- | --- | --- |
| C, 45.52; | H, 5.18; | N, 18.96 |
| Found: C, 45.38; | H, 5.32; | N, 18.79. |

Example 8

8-(Cinnamylmercapto)guanosine (22359)

Following the procedure for the preparation of 8-(2-propenylmercapto)guanosine (Example 6), but substituting cinnamyl bromide for allyl bromide, the title compound was obtained in 33 percent yield as an off-white powder, mp 172° C. (decomp.). NMR (DMSO-d$_6$): δ7.25 (br, 5H); 6.7-6.2 (m, 4H); 5.7 (d, J=5Hz, 1H). IR (KBr): 1690, 1640 and 1600 cm$^{-1}$.

| Analysis calculated for C$_{19}$H$_{21}$N$_5$O$_5$S: | | |
| --- | --- | --- |
| C, 52.89; | H, 2.91; | N, 16.23 |

| -continued | | |
| --- | --- | --- |
| Analysis calculated for C$_{19}$H$_{21}$N$_5$O$_5$S: | | |
| Found: C, 53.26; | H, 4.90; | N, 16.08. |

Example 9

1-Amino-7-(2,3-epoxypropyl)-8-oxoguanosine

Following the general procedure of step 1 of Example 1, using epibromohydrin as the alkylating agent, the title compound was obtained as a crude product. No purification was attempted.

Example 10

7-[2-Hydroxy-3-(phenylthio)propyl]-8-oxoguanosine hemihydrate (24331)

A mixture of the crude product of Example 9 (3 g, 5.4 mM and thiophenol (5 g, 45.4 mM) in DMF (150 ml) was heated at a bath temperature of 80° C. for a period of 4 hours. Following cooling, removal of most of the solvent in vacuo, dissolution of the residue in water and purification by preparative reverse phase HPLC (C-18), the 1-amino derivative of the title compound was obtained as an off-white powder in 52 percent yield, mp 135°-137° C. NMR (DMSO-d$_6$): δ7.3 (m, 5H); 7.15 (bs, 2H); 5.6 (d, J=5Hz, 1H); 5.35 (s, 2H). IR (KBr) 1700 and 1580 cm$^{-1}$.

Following the deamination procedure of step of Example 1 using the above-prepared 1-amino derivative, the title compound was prepared in 45 percent yield as a brown solid, mp 180°-182° C. NMR (DMSO-d6): δ7.3 (bs, 5H); 5.6 (bs, 2H); 5.7 (d, J=5Hz, 1H). IR (KBr): 1690, 1635, 1600 and 1100 cm$^{-1}$.

| Analysis calculated for C$_{19}$H$_{23}$N$_5$O$_7$S—½H$_2$O: | | |
| --- | --- | --- |
| C, 48.09; | H, 5.10; | N, 14.76 |
| Found: C, 48.16; | H, 5.11; | N, 15.04. |

Example 11

7-[3-(3,4-dimethyoxyphenethylamino)-2-hydroxy]-propyl-8-oxoguanosine monohydrochloride monohydrate (24364)

1-Amino-7-[3-(3,4-dimethoxyphenethylamino)-2-hydroxypropyl]-8-oxoguanosine (24330) was prepared in a manner analogous to the 1-amino derivative of Example 10 by substituting 3,4-dimethoxyphenethylamine for thiophenol. This 1-amino derivative was prepared in a 40 percent yield as an off-white powder, mp 156°-158° C. NMR (DMSO-d$_6$): δ7.0(bs, 3H); 6.9-6.4 (m, 3H); 5.3 (s, 2H); 3.7 (s, 6H). IR (KBr): 1670, 1615 and 1580 cm$^{-1}$.

Following the deamination procedure of step 2 of Example 1 (and Example 10) using the above-prepared 1-amino derivative, the title compound was prepared as a light brown powder in 55 percent yield, mp 163°-170° C. (decomp.). NMR (DMSO-d$_6$): δ8.9 (br, 1H); 6.8 (M, 5H); 5.6 (d, J=5Hz, 1H); 5.59 and 5.62 (both s, 3H each). IR (KBr): 1680, 1640, 1600 and 1030 cm$^{-1}$.

| Analysis calculated for C$_{23}$H$_{32}$N$_6$O$_9$—HCl—H$_2$O: | | |
| --- | --- | --- |
| C, 46.74; | H, 5.97; | N, 14.22 |
| Found: C, 46.85; | H, 6.01; | N, 14.25. |

Example 12

7-(3-Azido-2-hydroxypropyl)-8-oxoguanosine monohydrate (24670)

Following the procedure of Examples 10 and 11, 1-amino-7-(3-azido-2-hydroxypropyl)-8-oxoguanosine (24332) was prepared by reacting the crude epoxide of Example 9 with sodium azide. That 1-amino derivative was prepared in 35 percent yield as white crystals, mp 180°–182° C. (decomp.). NMR (DMSO-$d_6$): δ7.1 (bs, 2H); 5.6 (d, J=5Hz, 1H). IR (KBr): 2140, 1690 and 1550 cm$^{-1}$.

The title compound was obtained following the deamination reaction procedures of step 2 of Example 1 (and Examples 10 and 11) using the 1-amino derivative described immediately above (24332). The title compound was an off-white powder obtained in 30 percent yield, mp 138°–141° C. (decomp.). NMR (DMSO-$d_6$): δ6.4 (bs, 2H); 5.6 (d, J=5Hz, 1H). IR (KBr): 3600–3000, 2110, 1690 and 1660 cm$^{-1}$.

| Analysis calculated for $C_{13}H_{18}N_8O_7$—$H_2O$: | | |
|---|---|---|
| | C, 37.50; | H, 4.84; | N, 26.91 |
| Found: | C, 38.06; | H, 4.79; | N, 26.67. |

Example 13

7-(2,3-Dihydroxypropyl)-8-oxoguanosine monohydrate (24292)

Following the procedures of Examples 10–12, 1-amino-7-(2,3-dihydroxypropyl)-8-oxoguanosine (24457) was prepared by reacting the crude epoxide of Example 9 with water. That 1-amino derivative was obtained as an off-white powder in 55 percent yield, mp 210°–212° C. (decomp.). NMR (DMSO-$d_6$): δ6.9 (bs, 2H); 5.55 (d, J=4.5Hz, 1H). 5.3 (bs, 2H). IR (KBr): 1700, 1670 and 1600 cm$^{-1}$.

The title compound was obtained following the deamination reaction procedures of step 2 of Example 1 (and Examples 10–12) using the 1-amino derivative described immediately above (24457). The title compound was obtained as a white powder in 35 percent overall yield, mp 195°–196° C. NMR (DMSO-$d_6$): δ10.7 (bs, 1H); 6.5 (bs, 2H); 5.6 (d, J=5Hz, 1H). IR (KBr); 1680, 1640 and 1660 cm$^{-1}$.

| Analysis calculated for $C_{13}H_{19}N_5O_8$—$H_2O$: | | |
|---|---|---|
| | C, 39.90; | H, 5.41; | N, 17.90 |
| Found: | C, 39.67; | H, 5.32; | N, 17.52. |

Example 14

7-[3-[4-(4-Fluorophenyl)piperazinyl]-2-hydroxypropyl]-8-oxoguanosine hemihydrate (24455)

The title compound was prepared following the procedures of Examples 10–13 by reacting 4-(4-fluorophenyl)piperazine with the crude epoxide of Example 9, followed by deamination of the resulting 7-heteroatom-substituted-hydrocarbyl-1-amino derivative as is discussed in Examples 10–13. The title compound was obtained as a white powder in an overall yield of 25 percent, mp 178°–181° C. NMR (DMSO-$d_6$): δ6.8–7.1 (m, 4H); 6.3 (bs, 2H); 5.2 (d, J=5Hz, 1H). IR (KBr): 1690, 1600 and 1390 cm$^{-1}$.

| Analysis calculated for $C_{23}H_{30}FN_7O_7$—$\frac{1}{2}H_2O$: | |
|---|---|
| | C, 50.73; H, 5.74; N, 18.00 |
| Found: | C, 50.94; H, 5.76; N, 17.74. |

Example 15

7-[2-(4-Chlorophenyl)-2-oxoethyl]-8-oxoguanosine (23880)

Following the two-step procedure of Example 1, in which 2-bromo-4'-chloroacetophenone was used as the alkylating agent, the title compound was obtained in 35% overall yield as light brown powder, mp over 230° C. NMR(DMSO-$d_6$): δ10.7 (bs, 1H), 8.1 (d, J=10Hz, 2H), 7.7 (d, J=10Hz, 2H), 6.5 (bs, 2H), 5.6 (d, J=5Hz,1H), 5.3 (S, 2H). IR (KBr): 1700, 1680 and 1630 cm$^{-1}$.

| Analysis calculated for $C_{18}H_{18}Cl N_5O_7$ | |
|---|---|
| | C, 47.85; H, 4.02; N, 15.50 |
| Found: | C, 47.32; H, 3.98; N, 15.40 |

Example 16

7-(4-Nitrobenzyl)-8-oxoguanosine (23756)

Following the two-step procedure of Example 1, using 4-nitrobenzyl bromide as the alkylating agent, the title compound was obtained in 10% overall yield as a yellow powder, m.p over 230° C. NMR(DMSO-$d_2$): δ10.8(bs, 1H), 8.3(d, J=10Hz, 2H), 7.6 (d, J=10Hz, 2H), 6.5 (bs, 2H), 5.6 (d, J=5Hz, 1H). IR (KBr): 1680, 1640, 1600 and 1520 cm$^{-1}$.

| Analysis calculated for $C_{17}H_{18}N_6O_8$—$\frac{1}{2}H_2O$: | |
|---|---|
| | C, 46.11; H, 4.32; N, 18.98 |
| Found: | C, 46.48; H, 4.04; N, 18.72. |

Example 17

7-(4-Methoxybenzyl)-8-oxoguanosine (23890)

Following the two-step procedure of Example 1, using 4-methoxybenzyl chloride as the alkylating compound, the title compound was obtained in 7% overall yield as a beige powder, m.p. over 230° C. NMR(DMSO-$d_6$): 10.8(bs, 1H), 7.2 (d,J=10Hz, 2H), 6.8 (d. J=10H z, 2H), 6.4(bs, 2H), 5.5(d, J=5 Hz, 1H), 3.7(S, 3 H). IR(KBr): 1670, 1600, 1510, 1450 and 1250 cm$^{-1}$.

| Analysis calculated for $C_{18}H_{27}N_3O_7$—$\frac{1}{2}H_2O$: | |
|---|---|
| | C, 50.47; H,5.18; N, 16.35 |
| Found: | C, 50.85; H,5.12; N, 16.20. |

Example 18

7-(2-Chloroethyl)-8-oxoguanosine (24599)

The title compound was obtained following the general two-step synthesis of Example 1, in which chloroethyl bromide was used as the alkylating agent, in 27 percent yield as an off-white powder, mp 192° (decomp.). NMR (DMSO-$d_6$): δ9.8 (br, 1H); 6.9 (bs,2H); 5.8 (d, J=5Hz,1H). IR (KBr): 1680 and 1640.

| Analysis calculated for $C_{12}H_{16}ClN_5O_6$—$3/2H_2O$: | |
| --- | --- |
| | C, 37.07; H, 4.93; N, 18.02 |
| Found: | C, 36.65; H, 4.67; N, 18.18. |

Example 19

7-Heteroatom-substituted-hydrocarbyl-8-selenoxoguanosine Derivatives

7-Heteroatom-substituted-hydrocarbyl-8-selenoxoguanosine derivatives are prepared from suitably protected, corresponding 7-heteroatom-substituted-hydrocarbyl-8-thioxo derivatives whose preparations are discussed previously. Thus, the 7-heteroatom-substituted-hydrocarbyl-8-thioxoguanosine is reacted with an S-alkylating agent such as methyl iodide in a solvent such as DMSO. The S-alkylated product so obtained is thereafter reacted with sodium selenide to form the 7-heteroatom-substituted-hydrocarbyl-8-selenoxo derivative. The desired product can thereafter be obtained from the reaction mixture by reverse phase HPLC.

Example 20

7-(2-Allyl)-8-thioxoguanosine (22444)

The title compound was prepared from 8-(2-propenylmercapto)guanosine (22300; Example 6) using a rearrangement procedure.

Bistrimethylsilylacetamide (72 g, 354.7 mM) was added to a suspension of 8-(2-propenylmercapto)guanosine (20 g, 56.3 mM) as starting material in chloroform (500 ml), and the resulting mixture was heated at reflux for a period of 16 hours under $N_2$. After cooling, most of the solvent was removed in vacuo, and the residue was heated at 40° C. under vacuum for a period of 6 hours.

The oily residue was admixed with tetrahydrofuran (500 ml), $PdCl_2$ (10.3 g, 58.3 mM) and benzonitrile (12.1g, 117 mM), and the resulting admixture was heated at reflux under $N_2$ for 3 hours. That admixture was thereafter cooled to ambient room temperature, further admixed with pyridine (25 ml) and stirred overnight (about 16 hours). The admixture was filtered through silica gel and washed with methylene chloride ($2 \times 300$ ml). The combined filtrate was concentrated in vacuo, and the residue admixed with a mixture of water, methanol and acetic acid (500 ml; 10:10:1) and stirred for an additional time period of about 16 hours The majority of the added solvents was removed in vacuo, the residue was dissolved in DMF (1 liter), and then treated with charcoal. The suspension so obtained was filtered through a bed of Celite, and the filtrate concentrated in vacuo. The residue was treated with methanol and the resulting solid filtered, washed with acetone, and dried in an oven at 60° C. to provide 7-allyl-8-thioxoguanosine (8.5 g, 42.5 percent yield) as an off-white powder, mp above 230° C. NMR (DMSO-$d_6$): δ5.90 (m, 1H); 6.32 (d, J=5Hz, 1H); 6.56 (bs, 2H); 10.60 (bs, 1H). IR (KBr): 1700, 1635, 1605 and 1450 cm$^{-1}$.

| Analysis calculated for $C_{13}H_{17}N_5O_5S$: | |
| --- | --- |
| | C, 43.93; H, 4.82; N, 19.71 |
| Found: | C, 43.96; H, 4.87; N, 19.62. |

Example 21

7-Heteroatom-substituted-hydrocarbyl-8-cyanoimino-guanosine Derivatives

Corresponding 7-heteroatom-substituted-hydrocarbyl-8-thioxoguanosine derivatives are utilized as the starting materials for these derivatives. In a typical preparation, methyl iodide (42 mM) is added to 28 mM of the starting thioxoguanosine dissolved in dimethyl sulfoxide (DMSO). The addition takes place at room temperature and under nitrogen. The resulting admixture is stirred for about three hours and then cooled to about zero degrees C. Cyanamide (about 57 mM) is added followed by sodium hydride (60% oil dispersion; 5mM). That reaction mixture is permitted to warm to room temperature and is stirred for about one hour The reaction mixture is then poured into about 1.5 liters of diethyl ether and stirred for about 10 minutes. The ether layer is decanted, the residue extracted with a further 1.5 liters of diethyl ether additionally containing about 50 ml of acetic acid. The ether layer is again decanted and the residue is dissolved in water (about 500 ml). The desired compound is purified from the water layer by reverse phase HPLC (C-18).

Example 22

Lower Alkylidenedioxy Derivatives

A lower alkylidenedioxy derivative of one of the before-described compounds is exemplified by the following synthesis of an isopropylidene derivative.

A mixture of 7-heteroatom-substituted-hydrocarbyl-8-oxoguanosine (17 mM), 2,2-dimethoxypropane (41 mM), acetone (200 ml) and concentrated sulfuric acid (10 drops) are stirred under $N_2$ at ambient room temperature for a time period of 52 hours. The mixture is cooled to zero degrees C and treated with concentrated ammonium hydroxide (5 ml). The majority of the liquid is removed in vacuo, and the resulting solid is filtered. The filtered solid is washed with water, acetone, and then diethyl ether, followed by drying in a vacuum oven at 60 degrees C to provide the desired derivative. Similar procedures are followed for the 8-thioxo, 8-selenoxo and 8-cyanoimino derivatives.

Example 23

7-Heteroatom-substituted-hydrocarbyl-8-oxo-2',3'-O-isopropylidene-5'-benzoylguanosine A mixture containing an isopropylidene derivative as described in Example 22 (3mM), triethylamine (3 ml), benzoyl chloride (3 mM) and methylene chloride (100 ml) is stirred at ambient room temperature for a period of 16 hours. The mixture is thereafter poured into water, the methylene chloride layer separated, and the water layer extracted further with methylene chloride ($2 \times 150$ ml).

The methlene chloride layers are combined dried over $NaSO_4$, and the solvent removed in vacuo. The residue is purified by column chromatography on silica gel.

5'-Acetyl derivatives are prepared by substituting acetic anhydride for benzoyl chloride. 8-Thioxo, 8-selenoxo and 8-cyanimino derivatives are similarly prepared.

Example 24

7-Heteroatom-substituted-hydrocarbyl-8-thioxo-2',3',5'-triacetylguanosine

This preparation is exemplary of acylation procedures for the ribosyl ring 4-N,N-Dimethylaminopyridine (10 mg) is added to a mixture of the 7-heteroatom-substituted-hydrocarbyl-8-thioxoguanosine (3 mM), triethylamine (2 ml), acetic anhydride (15 mM; lower acyl chlorides or benzoyl chloride can be used in the alternative) and methylene chloride (50 ml). The resulting reaction mixture is stirred under $N_2$ for 16 hours at room temperature.

Further methylene chloride (50 ml) is thereafter added, and the solution is washed with 1N HCl, brine, and then water The solution is thereafter dried over $Na_2SO_4$. The solvent is removed in vacuo, and the residue is purified by column chromatography on silica gel.

Similar procedures are followed for the 8-oxo, 8-selenoxo and 8-cyanimino derivatives.

B. Exemplary Compositions For Administration

Exemplary solid and liquid compositions suitable for administering the compounds of the present invention are described below using five of the more preferred guanine nucleoside derivatives as exemplary active ingredients.

Tablets

Tablets are compounded from the following ingredients:

|  | Parts by Weight |
|---|---|
| 7-(2-chloroethyl)-8-oxoguanosine | 2.5 |
| Lactose, powdered | 36.4 |
| Corn starch, dry | 34.5 |
| Finely divided $SiO_2$ | 5.6 |
| Polyvinylpyrrolidone | 0.6 |
| Magnesium stearate | 0.4 |
|  | 80.0 |

The guanosine derivative is thoroughly admixed with the lactose, 25.0 parts by weight of the corn starch, and 4.0 parts by weight of the $SiO_2$. The resulting admixture is then uniformly moistened with a 5% ethanolic solution of polyvinylpyrrolidone. The moist mass is then passed through a one-millimeter mesh screen to produce a granulate. The produced granulate is dried for about 24 hours at 60° C. in a drying chamber. The dried granulate is again passed through a one-millimeter mesh screen. 70.0 Parts of the obtained granulate are admixed in a suitable mixer with a mixture consisting of the remainder of the $SiO_2$, the remainder of the corn starch and all of the magnesium stearate, which mixture previously had been passed through a one-millimeter mesh screen. The thus-obtained admixture is then pressed into tablets weighing 800 milligrams each and containing 25 milligrams of the guanosine.

Starch Capsules

Capsule contents are compounded from the following ingredients:

|  | Parts by Weight |
|---|---|
| 7-(carbethoxy methyl)-8-oxoguanosine | 10.0 |
| Lactose | 450.0 |
| Corn Starch | 540.0 |
|  | 1000.0 |

The guanosine derivative is gradually admixed with the lactose. When all of the lactose has been admixed, the obtained admixture is blended with the corn starch. The resulting blend is then filled into capsules holding 10 gram of the blend. Each capsule contains 1.0 milligrams of the guanosine derivative.

Tablets

A lot consisting of 10,000 tablets, each containing 50 milligrams of 7-(4-nitrobenzyl)-8-oxoguanosine is prepared from the following types and amounts of ingredients:

| 7-(4-nitrobenzyl)-8-oxoguanosine | 500 grams |
|---|---|
| Dicalcium Phosphate | 1000 grams |
| Methyl cellulose, U.S.P. (15 cps) | 75 grams |
| Talc | 150 grams |
| Corn Starch | 250 grams |
| Magnesium stearate | 25 grams |
|  | 2000 grams |

The guanosine derivative and dicalcium phosphate are mixed well, granulated with 7.5 percent solution of methyl cellulose in water, passed through a No. 8 screen (U.S. Standard Sieve Series) and dried carefully. The dried granules are passed through a No. 12 screen (U.S. Std. Sieve Series), mixed thoroughly with the talc, starch and magnesium stearate, and compressed into tablets.

Injectable Preparation

A sterile preparation suitable for subcutaneous or intracavitary injection and containing 50 milligrams of 7-carboxamidomethyl-8-oxoguanosine in each milliliter of ingredients is prepared from the following types and amounts of ingredients:

| 7-Carboxamidomethyl-8-oxoguanosine | 5 grams |
|---|---|
| Physiological saline | 98 milliliters |
| Sesame oil | 2 milliliters |

The guanosine derivative and saline are admixed and sonicated for a period of time sufficient to provide a substantially homogenous dispersion. The sesame oil is thereafter admixed and the new admixture is similarly homogenized to provide an emulsion. After emulsification, five to fifteen percent of the final volume of this sterile preparation are injected subcutaneously or intraperitoneally once a week to enhance humoral immunity.

Aqueous Preparation for Oral Use

An aqueous preparation for oral use containing in each 5 milliliters (1 teaspoon) 25 milligrams of 7-(4-methoxybenzyl)-8-oxoguanosine is prepared from the following ingredients:

| 7-(4-methoxybenzyl)-8-oxoguanosine | 5.0 grams |
|---|---|
| Methylparaben, U.S.P. | 0.75 grams |
| Propylparaben, U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water, q.s. to | 1000 milliliters |

C. Methods

Lymphocyte cultures. The serum-containing culture medium is prepared to contain the following per 100 milliliters: 91.9 milliliters RPMI 1640 (Flow Laboratories, Inc., Rockville, MD), 0.1 milliliters of 100×glutamine, 1.0 milliliter of 100×sodium pyruvate, 1.0 milliliter of 50×nonessential amino acids, 1.0 milliliter of water containing $10^4$ units of penicillin G and $10^4$ micrograms of streptomycin, and 5.0 milliliters of a supportive lot of fetal calf serum (FCS). These ingredients are admixed to apparent homogeneity. Spleen cell suspensions and populations enriched for splenic B cells are prepared as described in Goodman et al., *J. Immunol.*, 121:1905 (1978), For evaluation of the primary humoral immune response to sheep erythrocytes (SRBC), $5 \times 10^6$ to $10^7$ murine spleen cells are cultured in 1.0 milliliter of 5% FCS-containing medium for 4 or 5 days in the presence of immunogen. Cells are incubated in culture trays (Costar, Cambridge, MA) at 37° C. in a humidified atmosphere of 10% $CO_2$ in air using tissue culture boxes (CBS Scientific, Del Mar, CA) that are rocked at a frequency of 7 cycles per minute. Pooled SRBC are available from the Colorado Serum Co., Denver CO.

Human peripheral blood lymphocytes (PBL) are prepared from normal heparinized venous blood by Ficoll-diatrizoate density gradient centrifugation. PBL are depleted of suppressor T cells bearing the histamine type 2 receptor by adhering them to the surfaces of histamine-rabbit serum albumin-coated plastic petri dishes (Cell-ect No. 2 kit; Seragen, Boston, MA) and by recovering the nonadherent cells by panning as described by Wysocki and Sato, *Proc. Natl. Acad USA*, 75:2844 (1978) and modified by Cavagnaro and Osband, *Biotechniques*, January/February:30 (1983).

The tissue culture medium employed in these studies is prepared as follows: One hundred milliliters (ml) contained 87.9 ml RPMI 1640 (Flow Laboratories, Rockville, MD), 0.1 ml 100×glutamine, 1.0 ml of 1.0 M HEPES buffer (Microbilogical Associates, Bethesda, MD), 1.0 ml of water containing $10^4$U of penicillin G and $10^4$micrograms of streptomycin, and 10 ml of fresh autologous heat-inactivated plasma. For evaluation of the primary humoral immune response to SRBC, lymphoid cells are cultured at a density of $2 \times 10^6$/ml in a volume of 1.0 ml containing $5 \times 10^6$ SRBC as antigen (Colorado Serum Co., Denver, CO) together with IL-2 (a partially purified preparation of human IL-2 that is free of interferon-gamma activity was obtained from Electro-Nucleonics, Inc., Silver Spring, MD) and the guanine nucleoside derivative.

Assay of plaque forming cells (PFC). PFC secreting antibodies against SRBC are evaluated after 4 or 5 days of culture using a modification of the hemolytic plaque assay of Jerne and Nordin, *Science*, 140:405 (1963). The cells are brought up in complete medium before plaquing; they are plaqued in standard low $M_r$ agarose (Bio-Rad Laboratories, Richmond CA), and are incubated in SRBC-absorbed guinea pig complement for one hour after a 1.5 hour incubation without complement.

T Cell Replacing Activity $5 \times 10^6$ Viable CBA/CaJ mouse B cells are cultured. These cells are generated by sequentially treating spleen cells first with complement-fixing monoclonal antibodies directed against with thy 1.2 antigens of T cells and second with complement to lyse any T cells present (New England Nuclear, Boston, MA). The cells so treated are thereafter grown with or without 0.1 ml of 0.1 percent (v/v) SRBC as immunogen in serum-containing media further containing incremental amounts of a guanosine derivative ranging in amount from zero through $10^{-4}$ molar. Direct PFC to SRBC are determined 4 days thereafter.

Mice. CBA/CaJ mice, 8-16 weeks of age, are purchased from the Jackson Laboratory, Bar Harbor, ME. A breeding nucleus of CBA/N mice is provided by the Animal Production Section, National Institutes of Health, Bethesda, MD. All mice are maintained on Wayne Lab Blox F6 pellets (Allied Mills, Inc., Chicago IL) and chlorinated water acidified with HCl to a pH value of 3.0.

Cell preparations. Spleen and thymus cell suspensions are prepared as described in Goodman et al., J. Immunol, 121:1905 (1978). B cell-enriched populations are prepared by treating $10^8$ spleen cells with a 1:1000 dilution of monoclonal anti-thy 1.2 antibody (New England Nuclear, Boston, MA) for 30 minutes at 4° C. Treated cells are centrifuged at 280×gravity for 10 minutes, antibodies are removed, and the cells are resuspended in a 1:6 dilution of CBA RBC-absorbed guinea pig complement at 37° C. for 45 minutes Cells are then washed and cultured as described before.

Injections. Mice are injected i.p. with a solution containing 50 ug of TNP-BSA. Within about 30 minutes of the immunizing injection, two groups of six mice each also receive 0.2 ml i.p. injections of a guanosine of the invention in 100 percent sesame oil, or 2 percent (v/v) sesame oil sonicated in normal saline, with the guanosine being present at 5 mg/ml. A third group of six mice receive the immunization but no guanosine derivative. Anti-TNP-BSA antibody titers are thereafter determined using standard techniques.

The present invention has been described with respect to preferred embodiments. It will be clear to those skilled in the art that modifications and/or variations of the disclosed subject matter can be made without departing from the scope of the invention set forth herein

What is claimed is:

1. A substituted guanine nucleoside derivative that corresponds to the formula

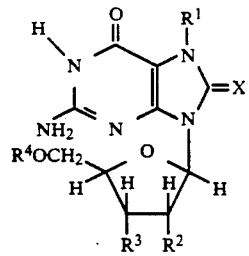

wherein

X is O;

$R^1$ is a heteroatom-substituted-hydrocarbyl radical selected from the group consisting of monohalo-substituted $C_2$ to $C_8$ alkyl, dihydroxy $C_3$ to $C_6$ alkyl, nitro substituted benzyl, $C_1$ to $C_6$ alkoxy substituted benzyl, and a $C_1$ to $C_6$ alkyl—O—(=O)—$C_1$ to $C_5$ alkylidene radical where the length of said radical is less than that of a decyl group;

$R^2$ and $R^3$ are the same or different radicals selected from the group consisting of hydrogen, hydroxyl, $C_1$ to $C_6$ alkoxy, lower alkanoyloxy, and benzoyloxy or $R^2$ and $R^3$ together constitute a $C_1$ to $C_6$ alkylidenedioxy radical;

$R^4$ is a radical selected from the group consisting of hydrogen, $C_1$ to $C_6$ alkanoyl, and benzoyl; and the pharmaceutically acceptable, non-toxic base addition salts thereof.

2. The substituted guanine nucleoside derivative of claim 1 wherein said $R^1$ radical has a length less than heptyl.

3. The substituted guanine nucleoside of claim 1 wherein $R^4$ is hydrogen.

4. The substituted guanine nucleoside derivative of claim 1 wherein $R^2$ and $R^3$ are hydroxyl, and $R^4$ is hydrogen.

5. The substituted guanine nucleoside derivative of claim 1 wherein $R^2$ and $R^3$ are hydroxyl and $R^4$ is hydrogen.

6. 7-Carbethoxymethyl-8-oxoguanosine.

7. 7-(4-Nitrobenzyl)-8-oxoguanosine.

8. 8-(4-Methoxybenzyl)-8-oxoguanosine.

9. 7-(2-Chloroethyl)-8-oxoguanosine.

10. 7-(2,3-dihydroxypropyl)-8-oxoguanosine.

11. A pharmaceutical composition a diluent amount of a physiologically tolerable carrier admixed with a compound of claim 1.

12. The composition of claim 11 wherein said $R^1$ radical has a length less than heptyl.

13. The composition of claim 11 wherein $R^2$ and $R^3$ are hydroxyl, and $R^4$ is hydrogen.

* * * * *

UNITED STATES PATENT AND TRADEMARK OFFICE
CERTIFICATE OF CORRECTION

PATENT NO. : 5,093,318

DATED : March 3, 1992

INVENTOR(S) : Michael G. Goodman et al.

It is certified that error appears in the above-identified patent and that said Letters Patent is hereby corrected as shown below:

Column 1, after the title and before the heading "CROSS-REFERENCE TO COPENDING APPLICATION", insert the following paragraph on line 6.

--This invention was made with government support under Contract Nos. AI 15284 and AI 07007 awarded by the National Institutes of Health. The government has certain rights in the invention.--

Signed and Sealed this

Thirteenth Day of December, 1994

Attest:

BRUCE LEHMAN

Attesting Officer    Commissioner of Patents and Trademarks